(12) United States Patent
Tamiya et al.

(10) Patent No.: US 7,362,433 B2
(45) Date of Patent: Apr. 22, 2008

(54) ABSORBANCE READER APPARATUS, ABSORBANCE READER CONTROL METHOD, AND ABSORBANCE CALCULATION PROGRAM

(75) Inventors: Eiichi Tamiya, c/o Tamiya Laboratory, School of Materials Science, Japan Advanced Institute of Science and Technology, 1-1, Asahidai, Nomi-shi, Ishikawa 923-1292 (JP); Toshiaki Tanaka, Tokyo (JP); Toshiki Morita, Tokyo (JP)

(73) Assignees: Hitachi Software Engineering Co., Ltd., Kanagawa (JP); Eiichi Tamiya, Ishikawa (JP)

( * ) Notice: Subject to any disclaimer, the term of this patent is extended or adjusted under 35 U.S.C. 154(b) by 385 days.

(21) Appl. No.: 10/550,004

(22) PCT Filed: Mar. 24, 2003

(86) PCT No.: PCT/JP03/03528

§ 371 (c)(1),
(2), (4) Date: Sep. 23, 2005

(87) PCT Pub. No.: WO2004/086010

PCT Pub. Date: Oct. 7, 2004

(65) Prior Publication Data

US 2006/0227320 A1    Oct. 12, 2006

(51) Int. Cl.
*G01J 3/42*    (2006.01)

(52) U.S. Cl. ............... 356/326; 356/328; 356/440

(58) Field of Classification Search ............ 356/326, 356/328
See application file for complete search history.

(56) References Cited

FOREIGN PATENT DOCUMENTS

| CA | 2 326 107 A1 | 3/1999 |
|---|---|---|
| JP | 47-45894 | 5/1971 |
| JP | 61-262639 | 9/1985 |
| JP | 01-307645 | 6/1988 |
| JP | 05-302893 | 6/1992 |
| JP | 06-323990 | 5/1993 |
| JP | 08-193945 | 1/1995 |
| JP | 08-304177 | 5/1995 |
| JP | 10-170429 | 10/1997 |
| JP | 2000-258341 | 3/1999 |
| JP | 2001-108525 | 10/1999 |
| JP | 2002-014044 | 6/2000 |
| WO | WO 99/08233 | 8/1998 |
| WO | WO 99/49973 | 3/1999 |
| WO | WO 00/17624 | 9/1999 |

OTHER PUBLICATIONS

International Search Report for Application Serial No. PCT/JP03/03528 dated Jul. 15, 2003.

*Primary Examiner*—F. L. Evans
(74) *Attorney, Agent, or Firm*—Reed Smith LLP; Stanley P. Fisher, Esq.; Juan Carlos A. Marquez, Esq.

(57) ABSTRACT

The absorbance of samples in a number of wells on a microchamber array is efficiently read in a short period of time. The microchamber array is simultaneously irradiated with monochromatic light. Well-transmitted light is captured via a telecentric optical system (23) by an imaging camera (24) as an image, and the absorbance of the sample in each well is individually calculated.

4 Claims, 23 Drawing Sheets

ABSORBANCE READER APPARATUS, ABSORBANCE READER CONTROL METHOD, AND ABSORBANCE CALCULATION PROGRAM

TECHNICAL FIELD

The present invention relates to an apparatus for measuring the absorbance of samples, and more particularly to an apparatus for measuring the absorbance of a sample injected into each of a number of wells provided on a microchamber array.

BACKGROUND ART

Absorbance reading apparatus according to the prior art typically reads the absorbance of a biological sample, such as a cell or nucleic acid, by placing the tested sample in a case called cell.

FIG. 24 illustrates the concept of a conventional absorbance reading apparatus. As shown, a sample solution that is to be read is placed in a cell. Irradiation light emitted by a light source is converted into monochromatic light by a spectroscope that is controlled by a wavelength drive unit. The monochromatic light is focused by a lens A into the sample, thus irradiating the sample. Light transmitted by the sample is condensed by a lens B and then converted into an electric signal by a detector.

Such an absorbance reading apparatus is only capable of reading the absorbance of one biological sample at a time. The cell is about 50 mm in height, 10 mm in width, and 10 mm in depth, so that a great amount of sample is required for reading. In another example, the absorbance of a specimen (sample) is measured in a nozzle (See JP Patent Publication (Kokai) No. 2000-258341 A, for example).

In these conventional absorbance reading apparatus, it has been difficult to read the absorbance of a number of samples efficiently in a short period of time because the samples have to be read in cells.

It is therefore an object of the invention to realize an absorbance reading system that can read the absorbance of many kinds of samples in small quantities in a short period of time at once. It is another object to realize data processing whereby data can be processed such that the visual observation of the absorbance that has been read can be facilitated and the results can be output in an easy-to-understand manner. A further object of the invention is to provide an absorbance reading system that enables a desired sample to be recovered for more detailed analysis based on the reading result of absorbance.

In accordance with the invention, a number of wells on a microchamber array are simultaneously irradiated with monochromatic light. Parallel light transmitted by the wells is captured via a telecentric optical system by an imaging camera as an image, and the absorbance of a sample in each well is individually calculated.

The invention provides an absorbance reading apparatus comprising: a sample base for mounting the microchamber array; a light source; a spectroscope on which light from the light source is incident; an irradiation optical system for adjusting the distribution of luminance of irradiation light emerging from the spectroscope; a field lens for enlarging the size of irradiation light transmitted by the irradiation optical system and irradiating the microchamber array mounted on the sample base with the enlarged irradiation light; a one-side telecentric optical system for receiving sample-transmitted light; and an imaging camera for producing image data based on the sample-transmitted light received via the one-side telecentric optical system. Irradiation light transmitted by the irradiation optical system is irradiated onto the microchamber array from an upper plane to a lower plane thereof, or from the lower plane to the upper plane thereof, passing through the wells in a depth direction. The absorbance reading apparatus may be provided with a sample recovery mechanism for recovering the samples in the wells. The absorbance reading apparatus according to the invention is capable of reading the absorbance of all of the wells on the microchamber array within one minute.

In order to read the absorbance of a plurality of samples injected into individual wells provided on a microchamber array, the invention, as the steps of controlling an absorbance reading apparatus, comprises: controlling a light source for emitting irradiation light for reading absorbance; selecting an absorbance read mode from the group consisting of a wavelength scan mode and a chronological scan mode; controlling a spectroscope for selecting the wavelength of the irradiation light; controlling an imaging camera for reading the absorbance of a sample; and storing the absorbance read by the imaging camera in a database. More specifically, the invention comprises the steps of: setting an exposure time of the imaging camera for reading the absorbance of a sample; setting a read start wavelength of the irradiation light for reading absorbance; setting a read wavelength resolution of the irradiation light for reading absorbance; setting a read time for reading absorbance; and setting the number of times of reading absorbance.

The invention preferably comprises the steps of: reading a zero-correction solvent; and reading a tested sample. The invention also comprises the steps of: specifying image data for calculating absorbance out of absorbance calculation image data read by the absorbance reading apparatus; specifying an absorbance calculation region in the specified image data; and calculating absorbance based on the specified absorbance calculation region. The step of specifying the image data for the calculation of absorbance comprises the steps of: displaying, as the image data, an image of the microchamber array in which a zero-correction solvent is placed and an image of the microchamber array in which a tested sample is placed; and specifying an absorbance calculation region on the image data of either the zero-correction solvent or the tested sample. Further, the invention may comprise an optical path length correction step of correcting absorbance reading apparatus-dependent differences in the optical path length on the tested sample, or the step of recovering a desired tested sample. The absorbance reading apparatus may be controlled by a computer program.

BEST MODE FOR CARRYING OUT THE INVENTION

The invention will be described in more detail by referring to the attached drawings.

Figure 1:
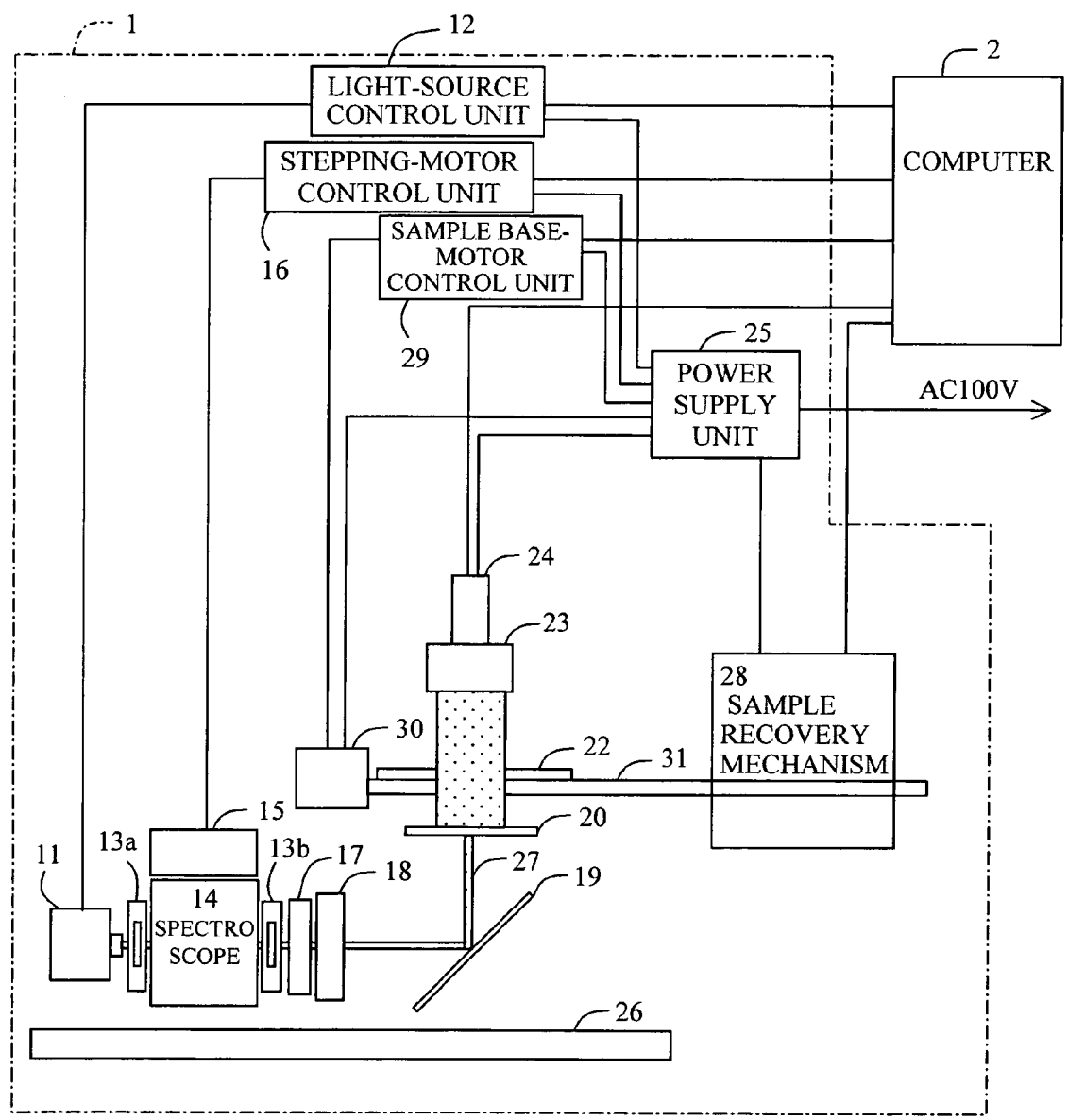
FIG. 1 shows a diagram of an absorbance reading system.

FIG. 1 shows a system configuration of the absorbance reading system according to the invention. The absorbance reading system is roughly comprised of an absorbance reading unit 1 for reading an image as the basis for calculation of absorbance, and a computer 2 for controlling the absorbance reading unit 1 and computing absorbance based on the image that has been read.

Referring to FIG. 1, the absorbance reading unit 1 will be described.

The absorbance reading unit 1 is comprised of a light source 11, a light-source controller 12, slits 13a and 13b, a spectroscope 14, a wavelength drive unit 15, a stepping motor controller 16, a lens holder 17, an irradiation lens 18, a mirror 19, a field lens 20, a sample base 22, a light-receiving lens 23, a CCD camera 24, a power source 25, an optical bench 26, a sample base-motor controller 29, a sample base motor 30, a ball screw A31, and a sample recovery mechanism 28. The function of each of these major portions is as follows.

The light source 11 emits irradiation light 27 with which a microchamber array (see FIG. 16) is irradiated. In the microchamber array, array samples (tested samples) are placed, which will be described later and for which absorbance is to be read. The light source 11 is a halogen lamp (visible light, 150 W) in the present example. The light source 11 is turned on or off by the light source controller 12.

The spectroscope 14 produces light of a desired wavelength (monochromatic light) from the irradiation light emitted by the light source 11. The spectroscope 14 is controlled by the wavelength drive unit 15. The slits 13a and 13b are used in combination with the spectroscope 14. In the present apparatus, the slit 13b is 1 mm in width and 10 mm in length so that the half-value width of the wavelength of the monochromatic light is 5 nm. The spectroscope 14 includes a diffraction grating by which the light incident on the spectroscope is separated into light with individual wavelengths. By providing the slit 13b for the thus wavelength-wise separated light, only light of a desired wavelength can pass through the slit 13b, thus producing monochromatic light.

Figure 2:
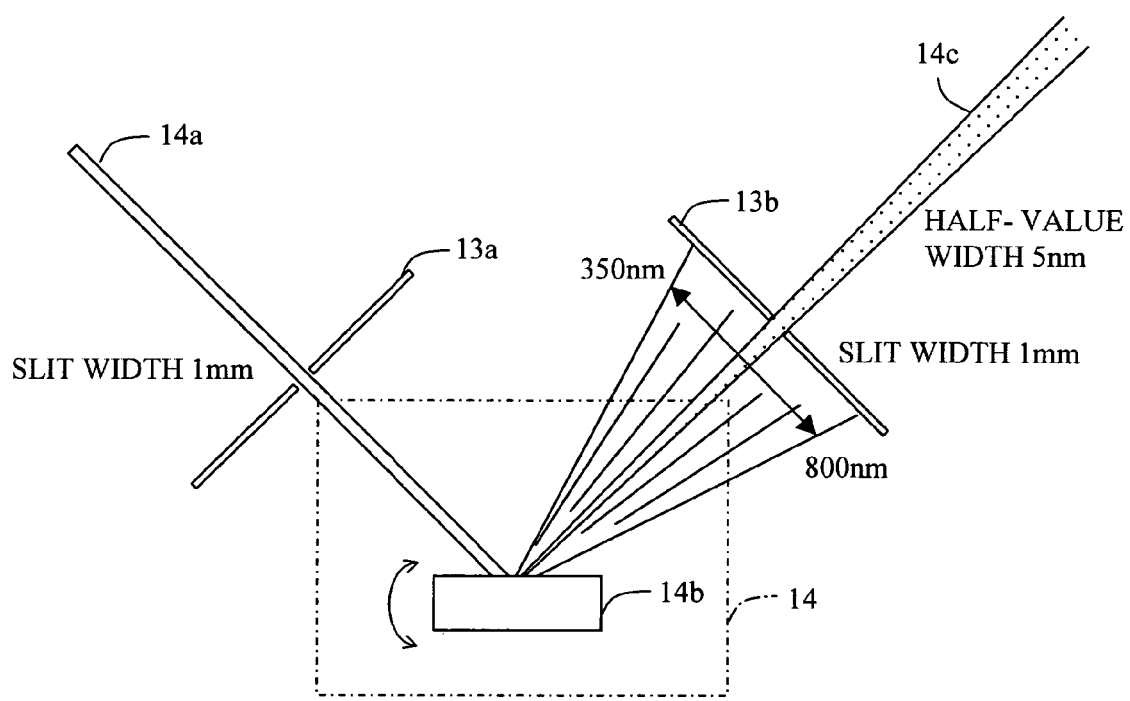
FIG. 2 shows a diagram illustrating wavelength separation by a spectroscope and a slit.

FIG. 2 shows the concept of wavelength separation by the spectroscope and the slits. A certain range of irradiation light 14a emitted by the light source 11 is passed by the slit 13a and it is then separated into light of wavelengths ranging from 350 nm to 800 nm by the diffraction grating 14b. The angle of the diffraction grating 14b is changed such that the slit 13b can pass a portion of the irradiation light, which ranges in wavelength from 350 nm and 800 nm, in units of a half-value width of 5 nm. The angle of the diffraction grating 14b is rotated by the wavelength drive unit 15.

The wavelength drive unit 15 is a motor for adjusting the angle of the diffraction grating 14b in the spectroscope, and is controlled via the stepping motor controller 16 by the computer 2. Thus, the wavelength of the irradiation light that leaves the spectroscope 14 can be controlled by the computer 2. In the present apparatus, the wavelengths in the range between 350 nm and 800 nm can be controlled with a wavelength resolution of 5 nm within one minute.

The lens holder 17 supports the irradiation lens 18. The irradiation lens 18 makes uniform the per-unit-area luminance distribution of the light that left the spectroscope 14. The lens reduces the detection sensitivity error in a read region. In the present apparatus, the light-quantity error in a 30×30 mm read region is controlled below 20% by the irradiation lens.

The mirror 19 guides the optical path upwards such that the sample is irradiated with the irradiation light vertically. While in FIG. 1 the mirror 19 guides the irradiation light upwards, the individual units on the light-receiving end, from the field lens 20 to the CCD camera 24 may be provided below the mirror 19, with the mirror guiding the optical path of the irradiation light downward. In this case, the absorbance of the sample is read below the mirror 19.

The field lens 20 enlarges the optical size such that the irradiation light 27 guided by the mirror 19 impinges on the entire reading surface. In the present apparatus, the optical size is enlarged by the field lens 20 from about 10 mm to about 30 mm.

Figure 3:
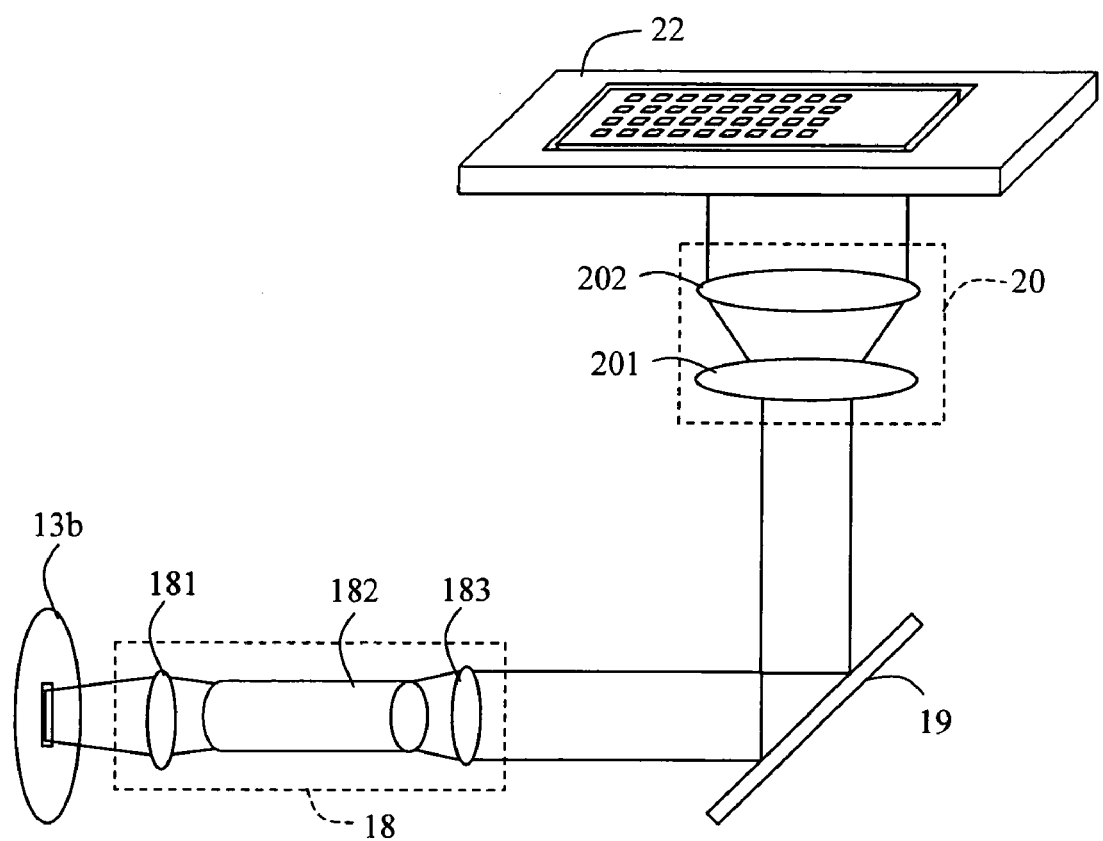
FIG. 3 shows a detailed diagram of an irradiation and light-receiving optical system.

Now referring to FIG. 3, the details of the optical system comprised of the irradiation lens 18 and the field lens 20 will be described.

The monochromatic light transmitted by the slit 13b is incident on the irradiation lens 18. The irradiation lens 18 is comprised of an incident-end lens 181, a rod lens 182, and an outgoing-end lens 183. In the present apparatus, the slit 13b is 1 mm in width and 10 mm in length. The light incident on the irradiation lens 18 is guided by the incident-end lens 181 into the rod lens 182. The rod lens 182 is a cylindrical lens made of glass. The incident light repeats total reflection within the rod lens 182, so that at the exit of the rod lens 182 the luminance distribution is uniform. The light going out of the rod lens 182 is condensed by the outgoing-end lens 183 and then guided to the mirror 19 and the field lens 20. In the present embodiment, the light as it leaves the slit 13b has a rectangular luminance distribution but is then converted by the irradiation lens 18 into circular light with uniform luminance distribution. Thus, the entire reading surface can be irradiated with uniform light with a luminance distribution of not more than 20%.

In the present apparatus, the incident-end lens 181 and the outgoing-end lens 183 each have a diameter of 10 mm. The rod lens 182 is 8 mm in diameter and 50 mm in length. The optical size of the light going out of the outgoing-end lens 183 is about 10 mm. The field lens 20 is comprised of two lenses, namely a lens A 201 and a lens B 202. The field lens 20 is a lens for enlarging the optical size so that the entire reading surface can be irradiated with the light. The size of light incident on the field lens 20, which is about 10 mm, is enlarged by the lens A 201 and lens B 202 into about 30 mm. The field lens 20 consists of two lenses so that the light leaving the field lens can be made closer to parallel light that can irradiate the sample more vertically.

Referring back to FIG. 1, the absorbance reading apparatus 1 will be described in more detail.

The light-receiving lens 23 receives light transmitted by the sample in a well. The light transmitted by the sample includes not only the light that has passed through the sample vertically but also the light that has undergone diffused reflection in the sample. However, in order to measure the sample-transmitted light, it is necessary to receive only the light that has passed through the sample vertically and not the light that has undergone diffused reflection in the sample. This is because the light that has experienced diffused reflection in the sample has not passed through the sample and makes it difficult to carry out correct absorbance measurement. Accordingly, in the present apparatus, a telecentric lens is employed as the light-receiving lens. A telecentric lens constitutes an optical system in which the principal ray on the object side and/or the image side do not intersect the optical axis until at an infinite point. For example, on the object side, the light from an object (principal ray) is parallel with the optical axis even outside the optical axis, namely the principal ray does not have a point of focus. In this case, the optical axis means the axis that passes through the center of the lens and that is vertical with respect to the lens. The case in which the light traveling from the lens to the image is parallel to the optical axis is called an image side telecentric, and the case where this occurs on either side is called both sides telecentric. In the present apparatus, a one-side telecentric lens is employed that has a point of focus on the CCD camera.

Referring to FIG. 4, the telecentric lens will be described.

Figure 4A:
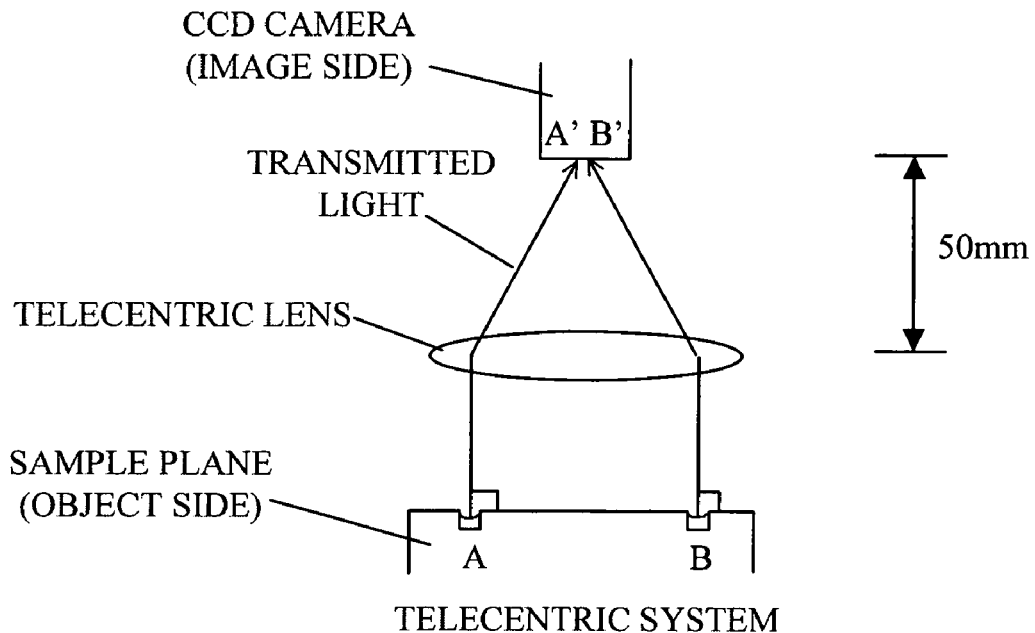
FIG. 4 shows diagrams illustrating a telecentric optical system.
Figure 4B:
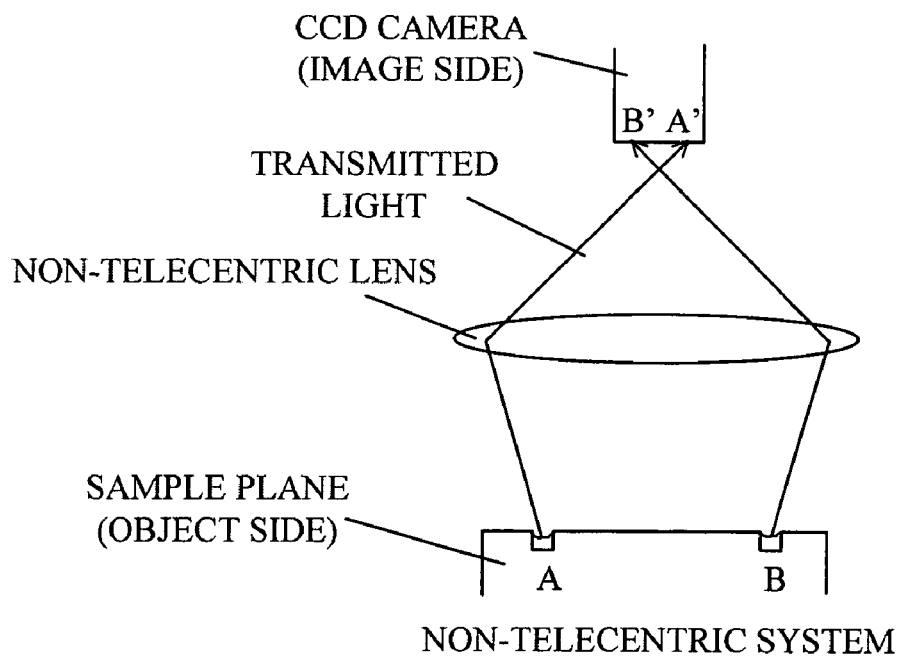

In FIG. 4(a), the light that vertically passes through the sample surface is condensed by the lens onto the CCD camera. In this case, it is possible to focus only the light that passes through the sample surface vertically on the CCD camera by using the one-side telecentric lens that has a point of focus on the CCD camera. On the other hand, if the transmitted light from the sample surface is focused on the CCD camera by a non-telecentric system as shown in FIG. 4(b), the light that is focused on the CCD camera is not the light that has passed through the sample surface vertically any more. In the present apparatus, a one-sided telecentric lens with a diameter of 30 mm (effective region diameter 27 mm) is employed. The focal distance between the one-sided telecentric lens and the CCD camera, which is dependent on the characteristics of the one-sided telecentric lens, is 50 mm in the present apparatus.

Referring back to FIG. 1, the absorbance reading apparatus 1 will be further described.

The CCD camera 24 detects the transmitted light received by the light-receiving lens 23 from the sample and then outputs image data. In the present apparatus, the CCD camera has about one million effective pixels (1,008×1,018). The exposure setting of the camera is based on an electronic shutter system (1/30 to 1/10,000), and the camera has 10-bit gradation.

The sample base motor 30 transports the sample base 20 horizontally and is controlled by the computer 2 via the sample base-motor controller 29. The ball screw 31 functions as rails for transporting the sample base 22 in a horizontal direction. The sample recovery mechanism 28 recovers a desired sample in the microchamber array placed on the sample base 22.

The power supply 25 supplies AC 100V electricity for the operation of the light source controller 12, the stepping motor controller 16, the sample base motor 30, the CCD camera 24, and the sample recovery mechanism 28. The optical bench 26 is a base on which the body of the absorbance reading apparatus 1 can be stably and securely mounted.

Thus, the absorbance reading apparatus 1 of the above structure can read a 30 mm×30 mm reading area with pixel resolution of 30 µm. It is also capable of reading an area ranging from 350 to 800 nm with wavelength resolution of 5 nm in about one minute. Thus, the absorbance of individual wells of 80 to several hundred µm can be read in great quantities and at once. Based on the reading results, it is possible to recover a sample in a desired well on the microchamber array as necessary.

Figure 5:
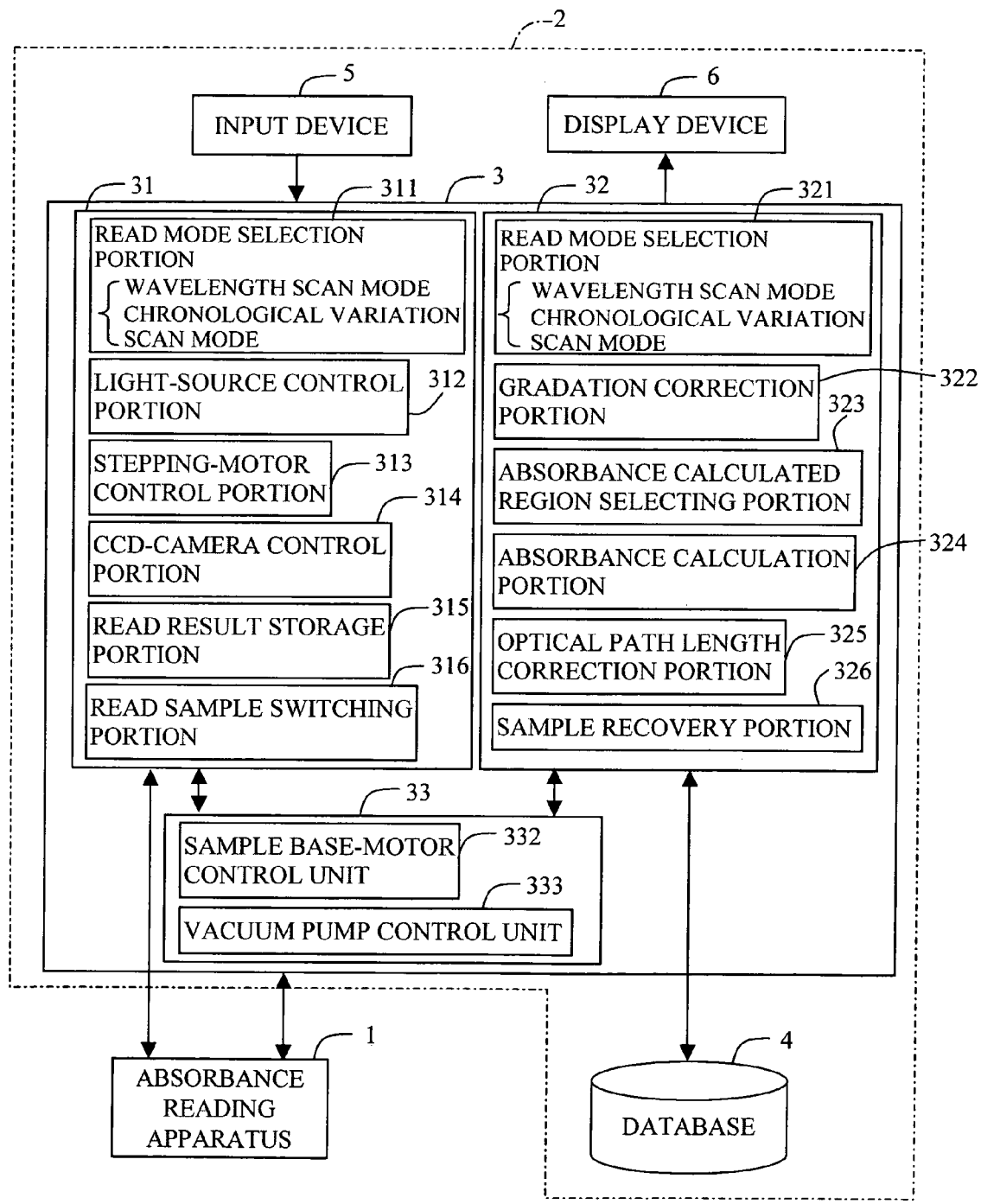
FIG. 5 shows a functional block diagram of a computer for controlling the absorbance reading apparatus.

Referring to FIG. 5, the outline of the process performed by a computer 2 in the invention will be described. The computer 2 controls the absorbance reading apparatus 1 and processes the calculation of absorbance, for example, based on the image read by the absorbance reading apparatus 1. The function or the like of its main parts is as follows.

An input unit 5 is a keyboard and mouse, for example, and is used by the operator for entering various instructions to the computer. A display unit 6 displays the results of processing by a computer program, GUI (Graphical User Interface) screens on which the operator can enter various instructions to the computer program on a dialog basis, or the results of calculation of absorbance. In a database 4, image data read by the absorbance reading apparatus 1 in a wavelength scan mode or a chronological-variation scan mode is stored. The database 4 also stores the results of calculation of absorbance, for example, based on the image data.

It is indicated in FIG. 5 that application programs including an absorbance reading program 31, an absorbance calculation program 32, and a sample recovery program 33 have been called to a processing unit 3 from a memory unit (not shown) such as a hard disc and are ready to be run.

The absorbance reading program 31 is mainly for controlling the absorption reading apparatus and reading image database on which absorbance is calculated. It is comprised of a reading mode selection portion 311 for selecting either the wavelength scan mode or the chronological-variation scan mode; a light source control portion 312 for controlling the light source 11 in the absorbance reading apparatus 1; a stepping motor control portion 313 for controlling a stepping motor; a CCD camera control portion 314 for controlling the CCD camera; a reading result storage portion 315 for storing the absorption reading results in the database 4; and a reading sample switching portion 316 for exchanging a zero-correction microchamber array and a microchamber array for tested samples.

The absorbance calculation program 32 is a program for mainly calculating absorbance based on the image data read by the absorption reading program 31 and displaying the results of calculation on a display unit 6. It is comprised of a read mode selection portion 321 for selecting the mode of absorbance calculation, that is either the wavelength scan mode or the chronological-variation scan mode; a gradation correction portion 322 for adjusting the luminance of a display image, for example; an absorbance calculation range selection portion 323 for selecting the well on the microchamber array on the basis of whose image absorption is to be calculated; an absorbance calculation portion 324 for calculating absorbance based on the designation of the read mode, the gradation correction, and the absorbance calculation range; an optical path length correction portion 325 for correcting the difference in optical path lengths between the conventional, commercially available absorption spectroscope and the apparatus of the invention; and a sample recovery portion 326 for recovering a sample in a desired well based on the result of calculation of absorption in accordance with an operator's instruction.

The sample recovery program 33 is a program for exchanging a zero-correction microchamber array and a microchamber array for tested samples, or for recovering a sample in a desired well on the microchamber array as designated by the absorbance calculation program 32, mainly in accordance with an instruction from the absorption reading program 31. The sample recovery program 33 includes a sample base-motor control portion 332 and a vacuum pump control portion 333.

Figure 6:
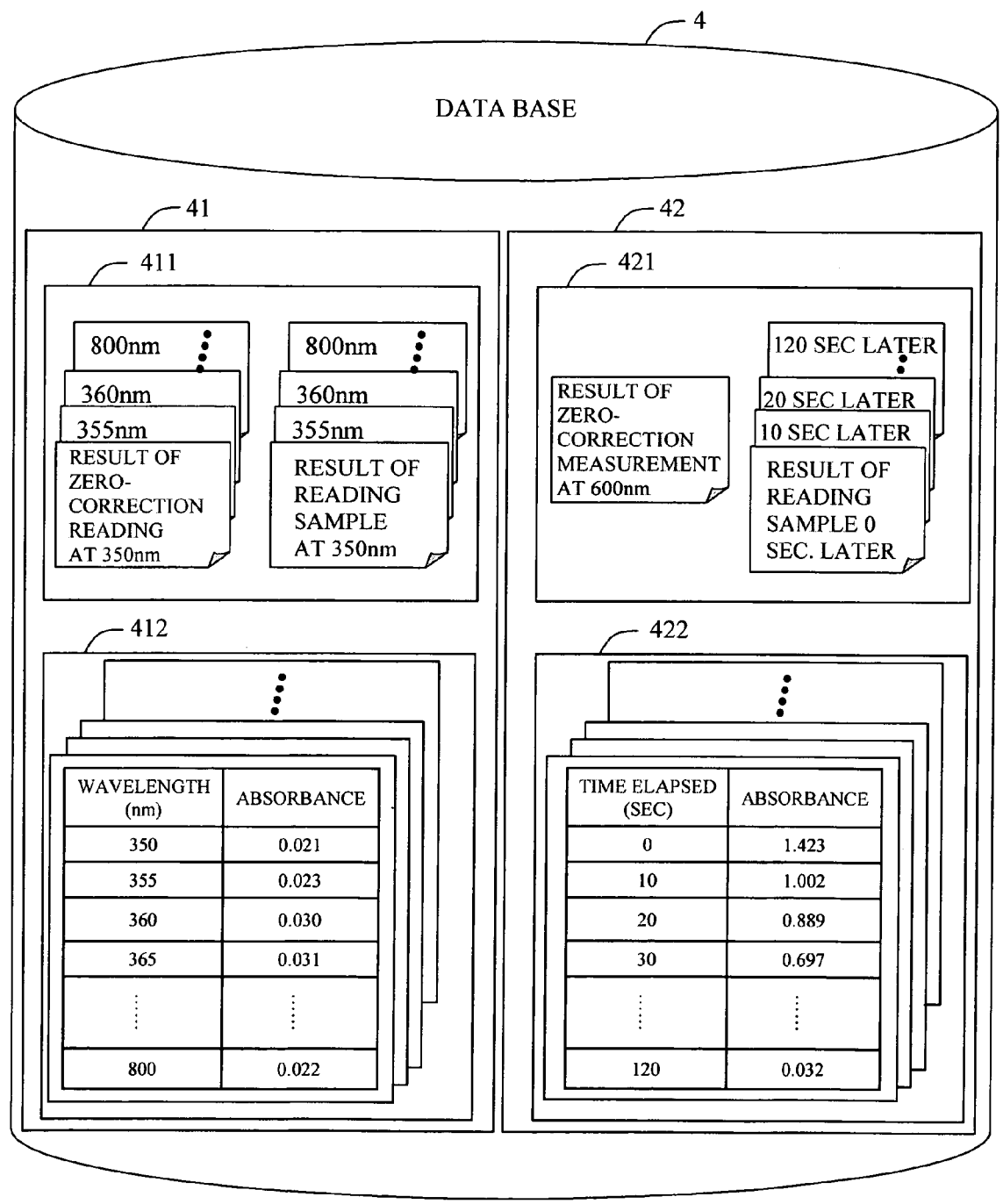
FIG. 6 shows a diagram of a database.

FIG. 6 shows an example of the database in which the results of reading and calculating absorbance in the absorption reading system are stored.

The database 4 is comprised of a wavelength scan mode file 41 and a chronological-variation scan mode file 42. In the wavelength scan mode file 41, a reading result 411 read in the wavelength scan mode and an absorbance calculation result 412 calculated on the basis of the reading results 411 are stored. In the chronological-variation scan mode file 42, a reading result 421 read in the chronological scan mode and an absorbance calculation result 422 calculated on the basis of the reading result 421 are stored.

The wavelength scan mode file 41 stores the result of zero-correction reading by the absorbance reading apparatus 1 at wavelengths in the range from 350 nm to 800 nm at 5 nm intervals, and the result of corresponding tested sample reading. It also stores the absorbance calculation result 412 concerning the absorbance at each wavelength calculated on the basis of the zero-correction read result and the tested sample read result.

The chronological variation scan mode file 42 stores the result of zero correction reading by the absorbance reading apparatus at a certain wavelength, such as 600 nm, for example, and the result of reading the tested sample at 600 nm at 10 second intervals from zero to 120 seconds. It also stores the absorbance calculation result 422 of calculating absorption at each elapsed time based on the result of the zero-correction reading result and the tested sample reading result.

Figure 7:
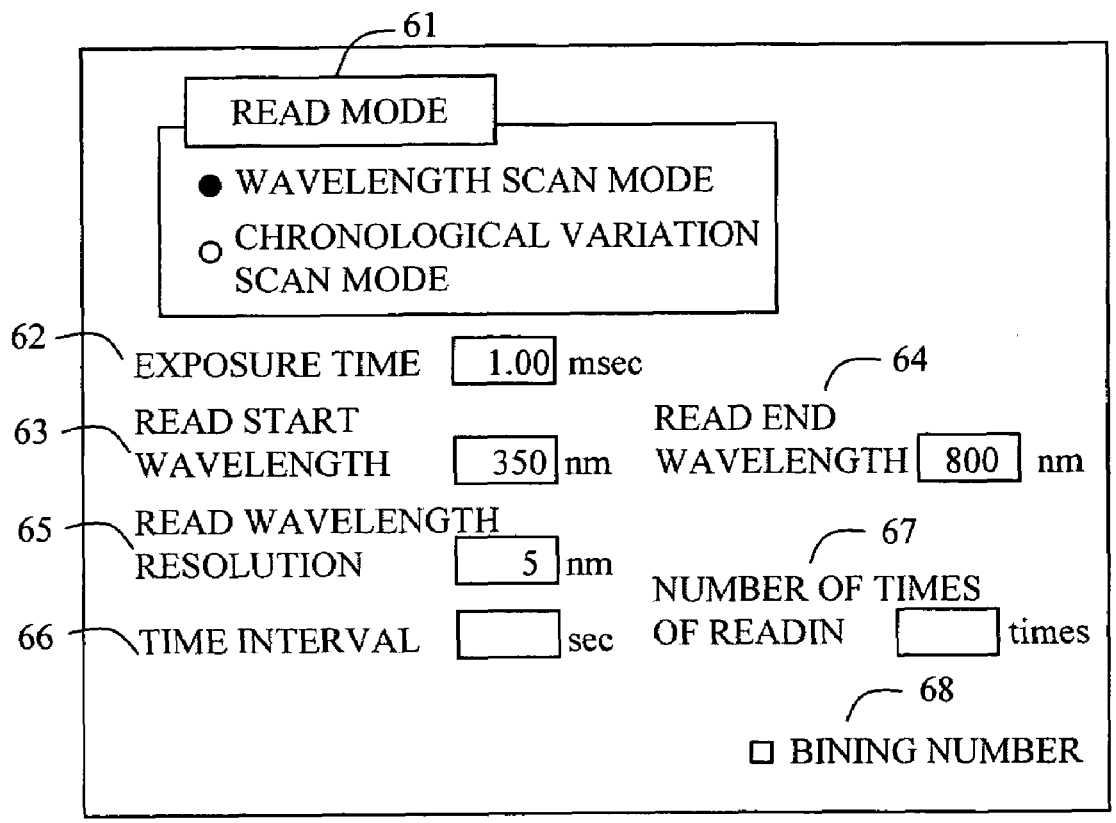
FIG. 7 shows an example of a read condition entry screen.

FIG. 7 shows an example of a screen for the entry of read conditions specified by the operator for the absorption reading program 31 shown in FIG. 5. In FIG. 7, a read mode 61 lets the operator select either a wavelength scan mode or a chronological-variation scan mode. In the example of FIG. 7, the wavelength scan mode is selected.

An exposure time 62 is the length of time of a single exposure of the CCD camera. In the present embodiment, it can be set between 0.1 to 30 msec at 0.1 msec units. The longer the exposure time, the greater the sensitivity of the CCD camera becomes, allowing for detection with less light. For example, when measuring a sample with a small transmittance, namely a sample with a high level of absorbance, the exposure time must be set long such as, for example, 30 msec. In the example of FIG. 7, the exposure time is set at 1 msec.

In the wavelength scan mode, a read start wavelength 63 and a read end wavelength 64 specify the wavelength at which a reading is initiated or ended. However, when the chronological-variation scan mode is selected, in which reading takes place at a single wavelength, the read start wavelength can be set but the read end wavelength cannot be set. In the example of FIG. 7, the read start wavelength is specified as 350 nm and the read end wavelength is specified as 800 nm.

A read wavelength resolution 65 specifies the intervals of read waveform between the read start wavelength to the read end wavelength, and it can be set only when the wavelength scan mode is selected. In the example of FIG. 7, the read wavelength resolution is specified as 5 nm. Thus, the wavelengths from the read start wavelength 350 nm to the read end wavelength 800 nm are read at 5 nm intervals. In the apparatus of the present embodiment, the read wavelength resolution can be selected from the choices of 5, 10, 15, and 20 nm. More detailed spectrum can be obtained with decreasing read wavelength resolutions, while the spectrum becomes coarser and the read time shorter with increasing read wavelength resolutions.

A time interval 66 and a read number of times 67 specify the time interval and the number of times of reading, respectively. They can be set only when the chronological-variation scan mode is selected. A bining number 68, when checked, specifies a 2×2 bining, and, when not checked, specifies no bining. A 2×2 bining refers to the process of averaging vertically and horizontally adjacent two pixels of the pixels obtained by a CCD camera and producing a single pixel. While the image resolution is doubled as a result, the file size can be advantageously reduced to one fourth the original size.

Hereafter, the calculation of absorbance will be described.

Figure 8:
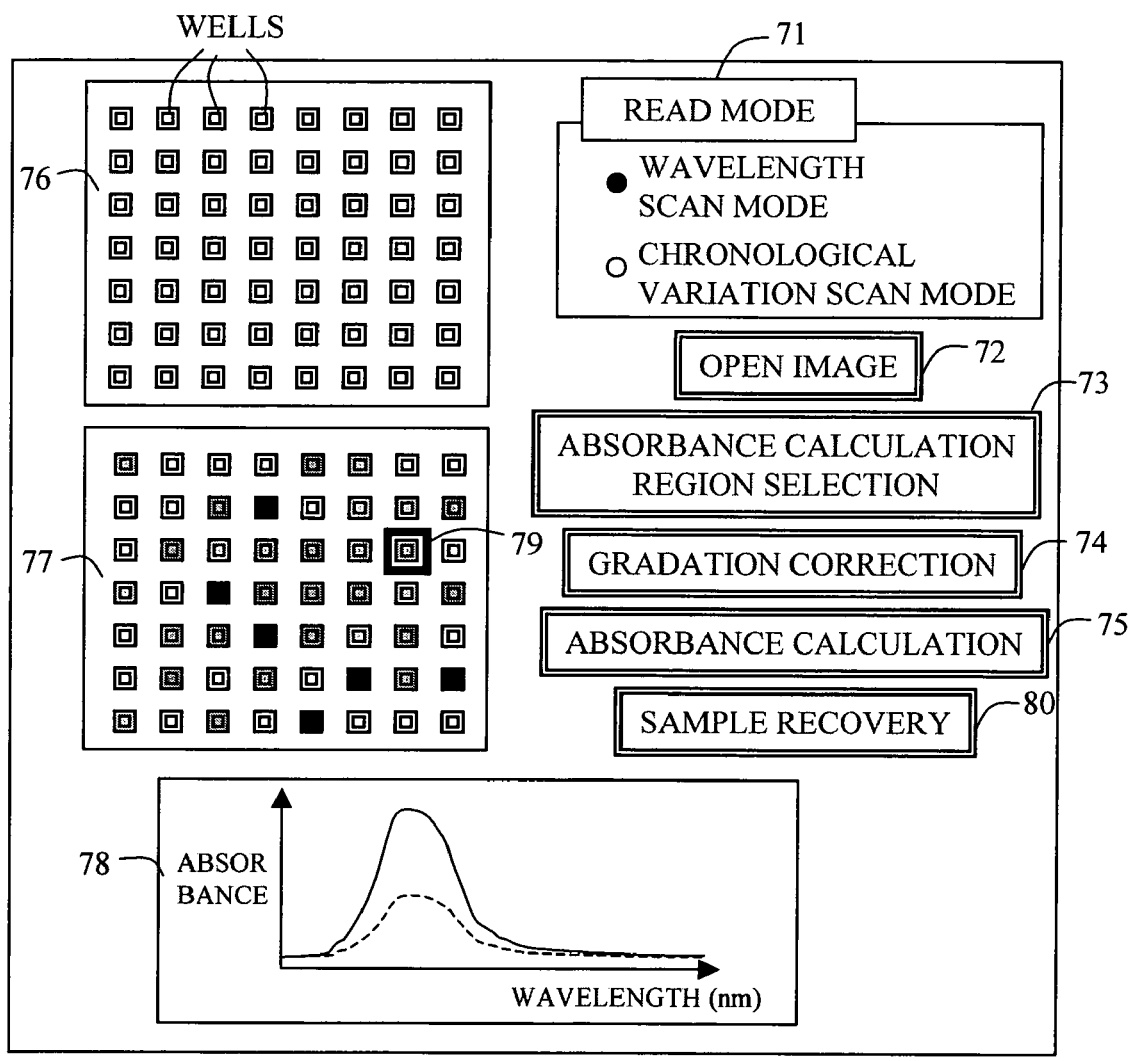
FIG. 8 shows a screen for the display of absorbance calculation conditions and the result of absorbance calculation.

FIG. 8 shows an example of a display screen on which the operator can specify absorbance calculation conditions for the absorbance calculation program 32 of FIG. 5. The screen can also display the result of calculation of absorbance by the absorbance calculation program 32, or allow the operator to instruct the recovery of a sample in a desired well on the basis of the result of calculation of absorbance.

In FIG. 8, a read mode 71 indicates that the wavelength scan mode has been selected. "Open an image" 72 is used in selecting an image from the zero-correction reading result images and sample reading result images stored in the database 4, based on which image absorbance is to be calculated. The selected image is displayed on a zero-correction display window 76 and a sample display window 77.

In the present embodiment, images are displayed in varying gradations such that pixels with high luminance are darkened (toward black) and pixels with low luminance are lightened (toward white). Thus, the user can easily recognize the positions of wells on the image. At the same time, all of the wells that are within the 30 mm-square read area are displayed. However, since the image resolution in the present apparatus is 30 μm, the length of each side of each well and the well interval must be 30 μm or more. In the present embodiment, the length of a side of a well must be at least 80 μm if absorbance is to be calculated accurately. This is because it is believed that at least three pixels must be provided for the display of a single well.

An absorbance calculation region selection 73 is for the selection of a region in a readout image for which absorbance is to be calculated. As an absorbance calculation region 79 is designated on the zero-correction display window 76 and the sample display window 77 using a mouse, the designated image is selected as the absorbance calculation region 79. By selecting one well as the absorbance calculation region 79, the absorbance of the single well can be calculated. Further, as it is possible to select the absorbance calculation region 79 as desired, the absorbance of a variety of sizes of wells (such as a well of 90 μm square) can be calculated. In the example of FIG. 8, it is indicated that a well in the second column from right and the third row from top is selected as the object of calculation of absorbance. In this case, the calculation of absorbance is conducted in association with a well in the zero-correction display window 76 in the second column from right and the third row from top. On the other hand, when a well is selected in the zero-correction display window 76, the calculation of absorbance is conducted in association with a corresponding well in the sample display window 77.

A gradation correction 74 is for the setting of an upper and a lower limit of gradation of a displayed image. By adjusting the luminance of the display unit by gradation correction, the luminance value of the image is enhanced so that the appearance of the image can be improved.

An absorbance calculation 75 is for the calculation of the absorbance of a region selected by the absorbance calculation region selection 73, and for the display of the result of calculation on an absorbance display window 78. For example, in the wavelength scan mode, the absorbance for each wavelength is calculated, and the result is plotted on the absorbance display window 78. At the same time, the wavelength and the result of calculation are stored in the database 4. This corresponds to the result of calculation of absorbance described with reference to FIG. 6. FIG. 8 shows the case of display in the wavelength scan mode. In the case of display in the chronological-variation scan mode, the horizontal axis indicates time and the vertical axis indicates absorbance.

A sample recovery 80 is for the activation of the sample recovery program 33 and the recovery of a sample in a desired well. As the sample recovery program is activated, the sample in a well selected as the absorbance calculation region 79 on the sample display window 77 is recovered.

Hereafter, the details of the absorbance read-out process will be described.

There are two modes of absorbance read-out, namely the wavelength scan mode and the chronological-variation scan mode. The wavelength scan mode is a read-out process in which the range of wavelengths from the readout start wavelength to the readout end wavelength are read at the readout wavelength resolution intervals, and then the absorbance for each wavelength is calculated. For example, when the readout start wavelength is 350 nm, the readout end wavelength is 800 nm, and the. readout wavelength resolution is 5 nm, readout is conducted at 350 nm, 355 nm, 360 nm, 365 nm, 370 nm, . . . , 795 nm, and 800 nm. The wavelength scan mode is generally used when the peak wavelength and the peak absorbance value of the absorbance spectrum are unknown.

Further, there are two types of readout, namely one on a zero-correction solvent and the other on the tested sample. This is so that the absorbance can be calculated based on the result of the zero-correction solvent and that of the tested sample.

Figure 9:
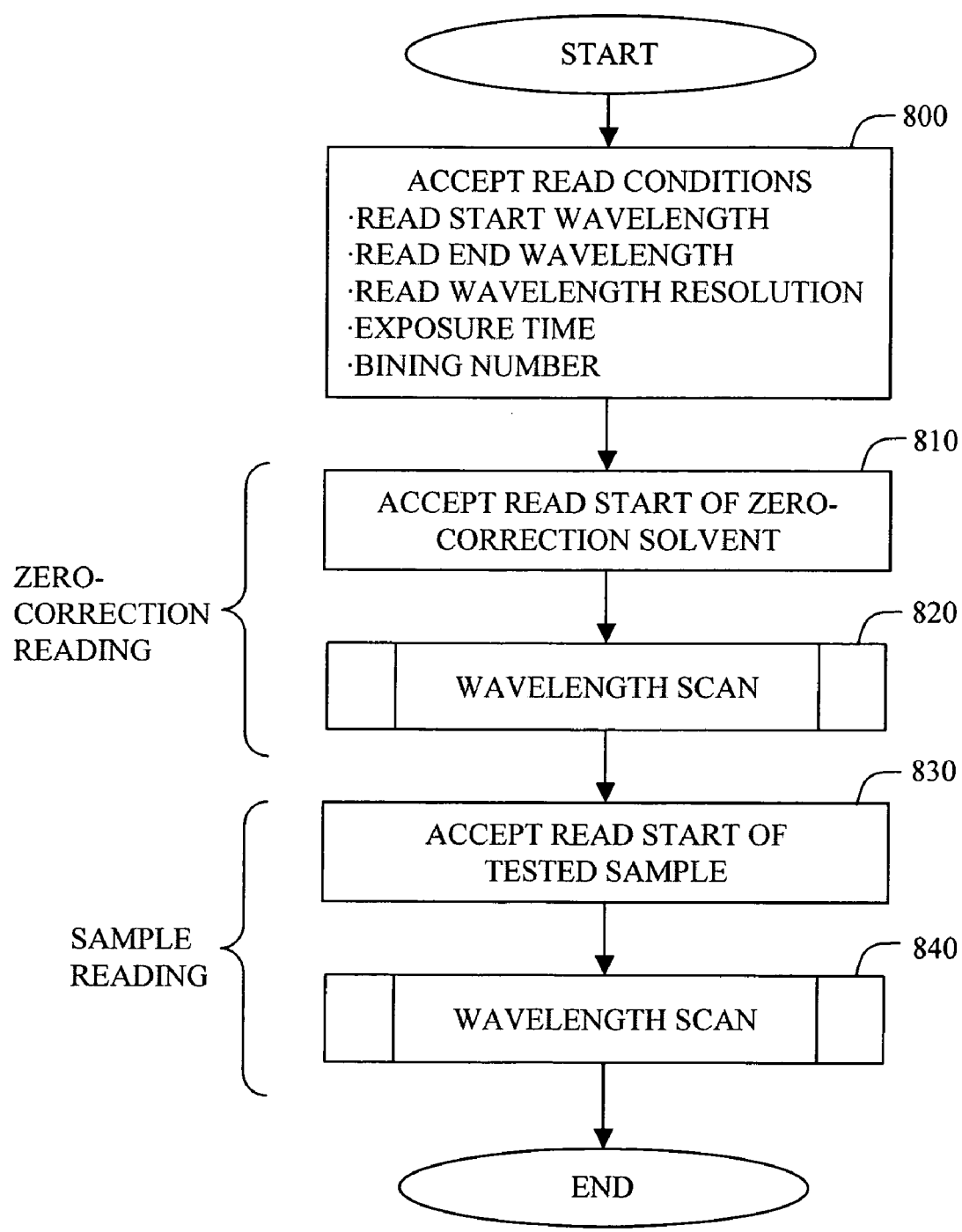
FIG. 9 shows a flowchart of a read process in a wavelength scan mode.
Figure 10:
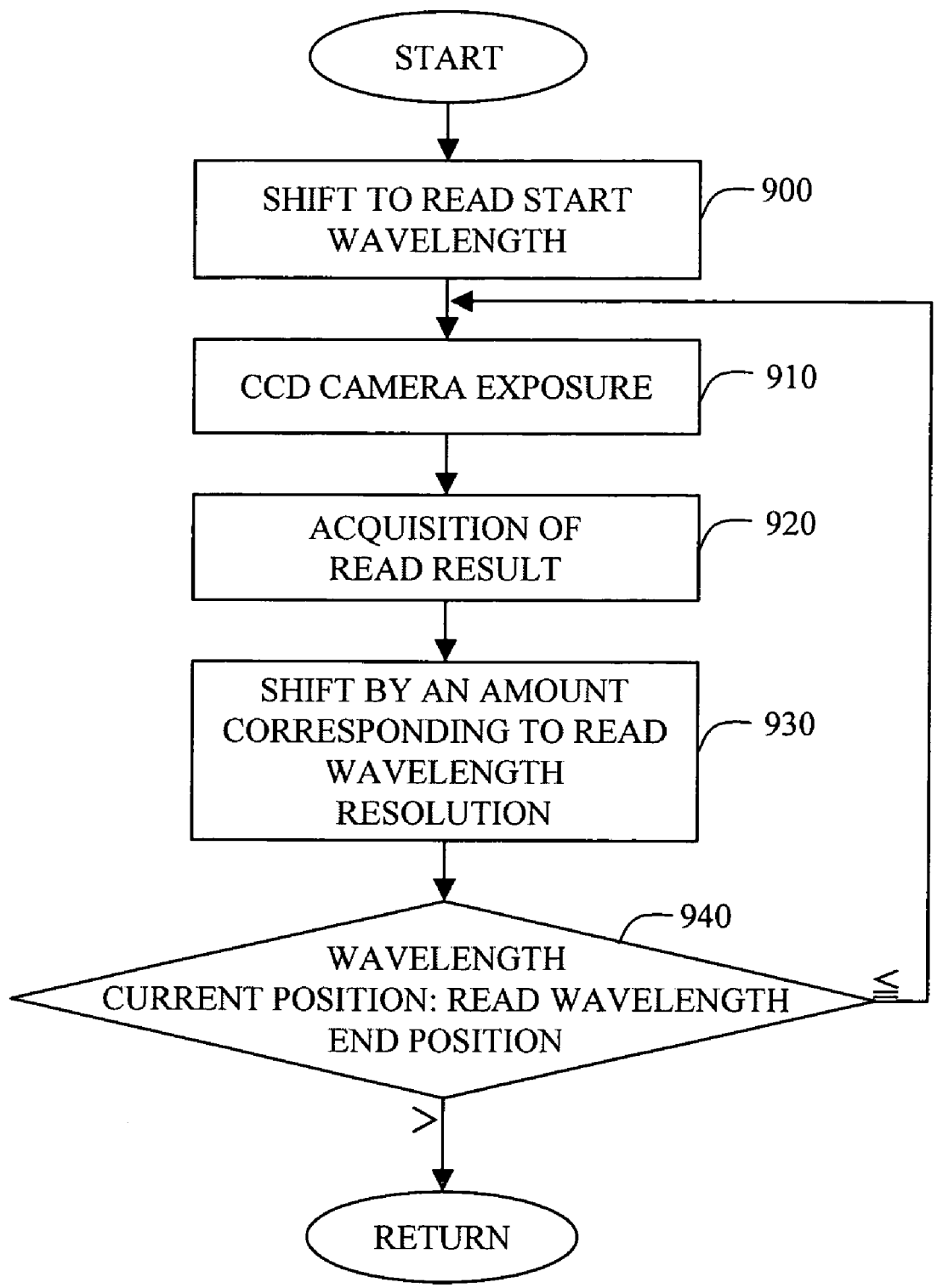
FIG. 10 is a flowchart of a wavelength scan.

FIG. 9 shows a flowchart of the absorbance readout program 31 in the wavelength scan mode. First, the operator sets a microchamber array of a zero-correction solvent and a microchamber array of a tested sample on the sample base 22. In the wavelength scan mode, the absorbance readout program 31 accepts the entry of readout conditions (readout start wavelength, readout end wavelength, readout wavelength resolution, exposure time, bining number) from the operator via the screen shown in FIG. 7 (step 800). Next, the program accepts the entry of initiation of readout of the microchamber array of the zero-correction solvent that is set on the sample base 22 (step 810). The program then carries out a wavelength-scan sub-routine shown in FIG. 10, thereby performing a wavelength scan of the zero-correction solvent (step 820). The process of wavelength scan is as shown in FIG. 10. After the start of the wavelength scan mode, the wavelength drive apparatus is moved up to the readout start wavelength accepted in step 800 of FIG. 9 (step 900). Thereafter, the CCD camera is exposed with the exposure time accepted in step 800 of FIG. 9 (step 910). Absorbance is then read by controlling the absorbance readout unit 1, and the result is stored in a database 411 (step 920). Then, the wavelength is shifted from the current wavelength position by a distance corresponding to the readout wavelength resolution (step 930). If the current wavelength of the spectroscope is equal to or smaller than the readout end wavelength in step 940, the routine returns to step 910 and the same process is repeated. If the current wavelength of the spectroscope is larger than the wavelength of the readout end wavelength in step 940, the wavelength scan comes to an end and the routine returns to step 820 of FIG. 8. Thus, steps 810 and 820 of FIG. 9 correspond to the readout of the zero-correction solvent.

Next, instead of the zero-correction solvent, the microchamber array of the tested sample is automatically set by a readout sample switching portion 316 at a readout position of the sample base 22, and then the entry of initiation of readout of the tested sample is accepted (step 830). Then, a wavelength scan is performed according to the wavelength scan processing program (FIG. 9) in step 840, which completes the readout process.

Hereafter, the details of the readout of absorbance in the chronological-variation scan mode will be described.

The chronological-variation scan mode is a mode in which the absorbance is calculated for each elapsed time at a single readout wavelength. For example, when the readout wavelength is 600 nm, the readout interval is 10 seconds, and the number of times of readout is 10, absorbance is read at the constant readout wavelength of 600 nm at 0, 10, 20, 30, . . . , and 100 seconds after the start of readout. The chronological-variation scan mode is generally used when the wavelength to be read is known and the variation of absorbance at that wavelength for each elapsed time is unknown.

Figure 11:
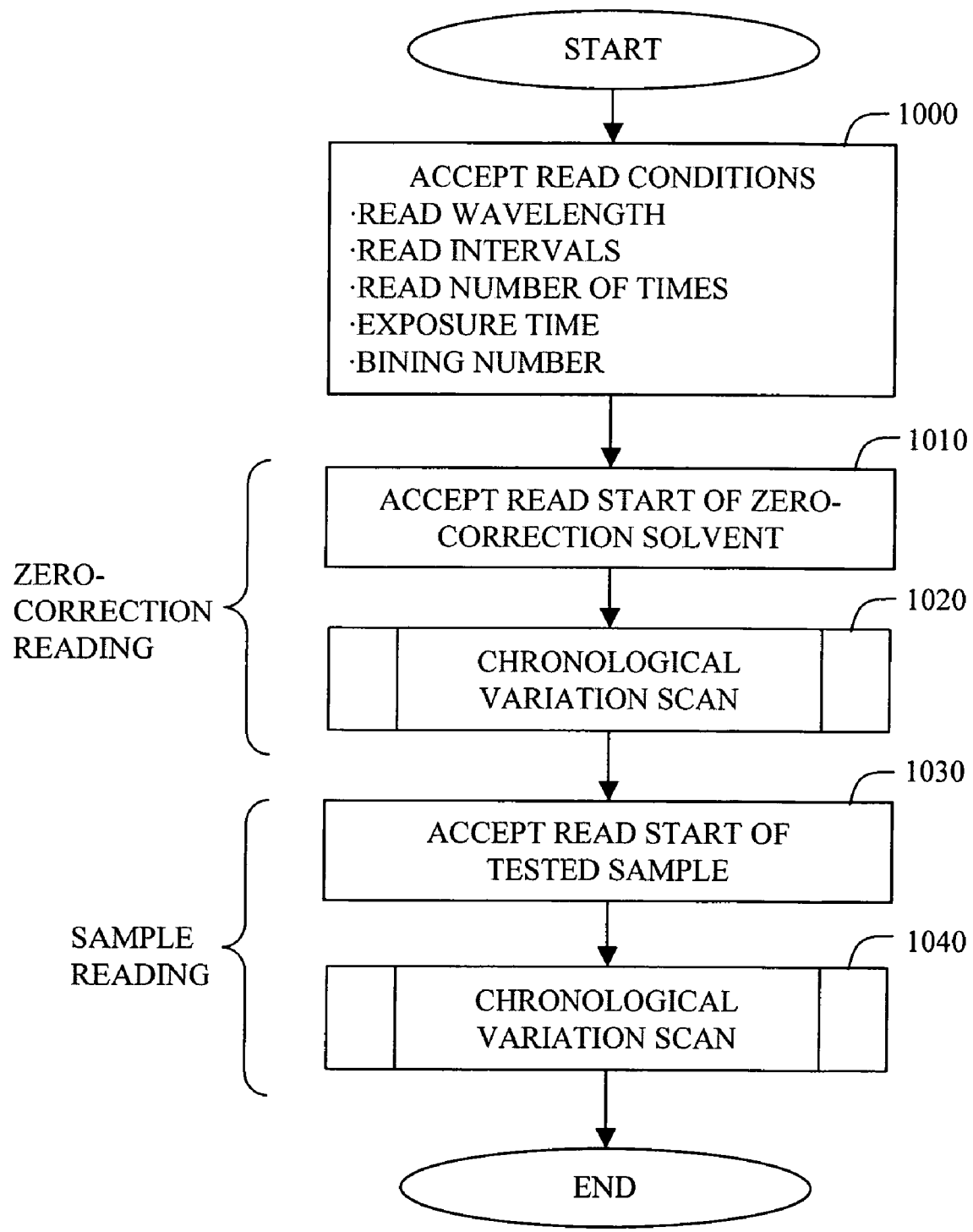
FIG. 11 is a flowchart of a read process in a chronological-variation scan mode.

FIG. 11 shows a flowchart of the process performed by the absorbance readout program 31 in the chronological-variation scan mode. The operator sets the microchamber array for the zero-correction solvent and the microchamber array for the tested sample on the sample 22 in advance. In the chronological-variation scan mode, after the start of readout, the absorbance readout program 31 accepts the entry of readout conditions (readout wavelength, readout interval, readout number of times, exposure time, bining number) from the operator via the screen shown in FIG. 7 (step 1000). Then, the program accepts the entry of initiation of readout from the operator (step 1010), and runs the sub-routine for chronological scan shown in FIG. 12, thus performing a reading (chronological variation scan) at the specific readout wavelength set (step 1020).

Figure 12:
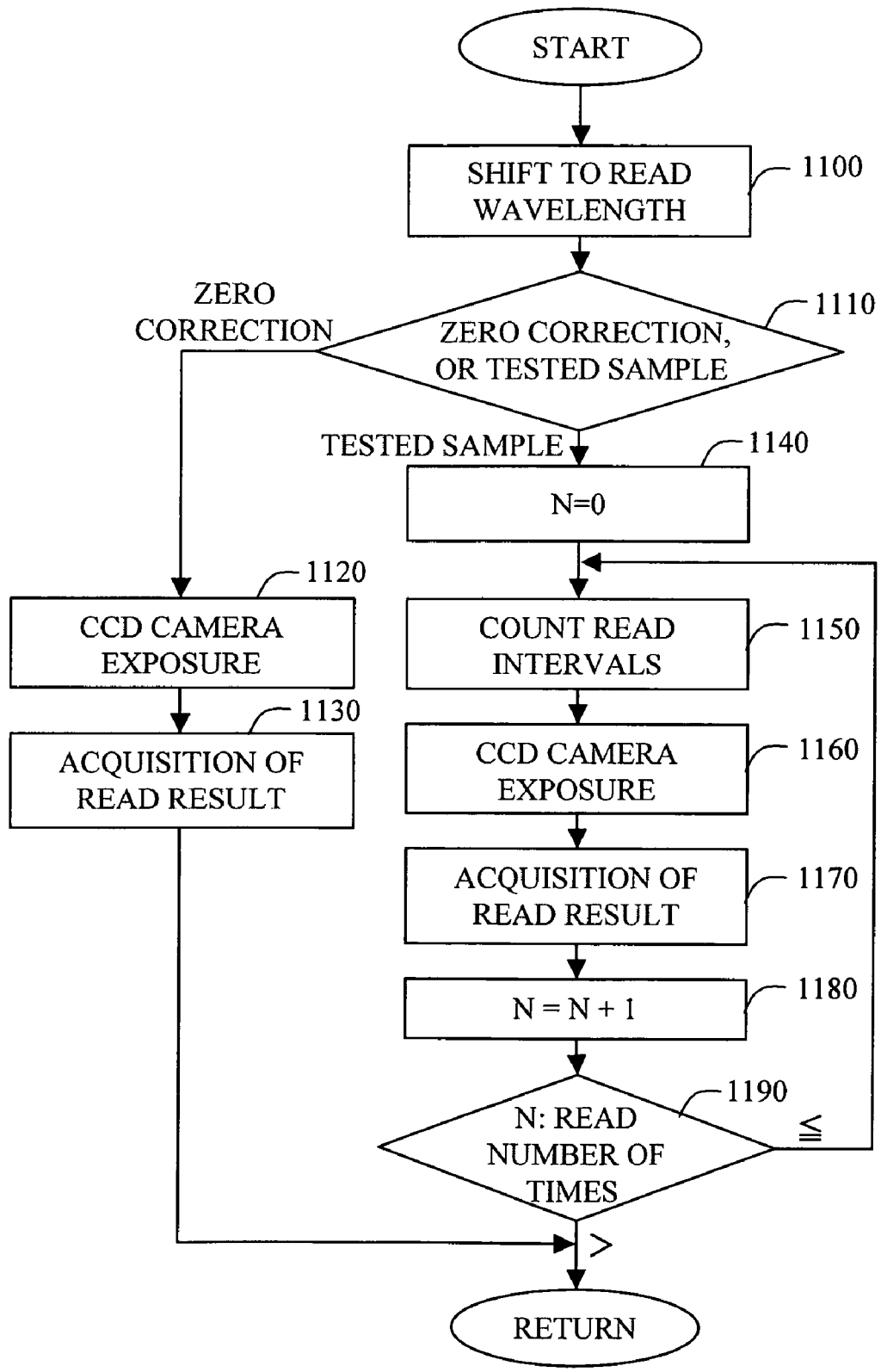
FIG. 12 is a flowchart of a chronological variation scan.

FIG. 12 shows a flowchart of the chronological variation scan. After the start of chronological variation scan, the wavelength of the spectroscope is shifted to the readout wavelength accepted in step 1000 of FIG. 11, under the control of the wavelength drive unit 15 (step 1100). Then, it is determined whether the readout is for the zero-correction solvent or the tested sample readout (step 1110). In the case of a readout of the zero-correction solvent, the CCD camera is exposed in step 1120. Thereafter, the absorbance of the zero-correction solvent is read by controlling the absorbance reading apparatus 1, and the result of readout is obtained and stored in a database 421 (step 1130). Then, the routine returns to step 1020 of FIG. 11. The zero-correction solvent is exchanged with the microchamber array for the tested sample and automatically set at a readout position on the sample base 22 by a readout sample switching portion 316, and the entry of readout of the tested sample is accepted (step 1030). Then, the sub-routine for chronological variation scan shown in FIG. 12 is executed, thus reading the sample at the specific wavelength set (chronological variation scan) (step 1040).

After the start of chronological variation scan of FIG. 12, the wavelength of the spectroscope is shifted to the readout wavelength accepted in step 1000 of FIG. 11, under the control of the wavelength drive unit 15 (step 1100). It is then determined whether the readout is for the zero-correction solvent or the tested sample (step 1110). If it is the readout of the tested sample, a variable N is made zero in step 1140. Then, the readout intervals accepted in step 1000 of FIG. 11 are counted (step 1150), the CCD camera is exposed (step 1160), the absorbance of the sample is read by controlling the absorbance readout apparatus 1, and the result of readout is obtained and stored in the database 421 (step 1170). Thereafter, 1 is added to N (step 1180), and it is determined whether the specified number of times of readout has been scanned (step 1190). If N is equal to or smaller than the readout number of times, the routine returns to step 1150 and the same process is repeated. If N is larger than the readout number of times, the chronological variation scan comes to an end and the routine returns to step 1040 of FIG. 11, and the process comes to an end.

Hereafter, the absorbance calculation process will be described in detail.

The absorbance calculation process is the process of calculating absorbance based on the images of the zero-correction solvent and the tested sample that have been obtained by the absorbance readout program 31 and then stored in the database 4. There are two modes of the absorbance readout process, that is the wavelength scan mode and the chronological-variation scan mode, of which the former will be described in the following.

Referring to FIG. 6, images corresponding to the wavelengths that have been read for the zero-correction readout result and the tested sample readout result are stored in the readout result 411 in the database 4. The absorbance calculation program 32 accepts the zero-correction readout result image and the tested sample readout image, and displays them in the zero-correction display window 76 and the sample display window 77, respectively, as shown in FIG. 8. Thereafter, the absorbance calculation program 32 accepts a desired absorbance calculation region selected by the operator, and displays it on the screen. Then, the average absorbance within the absorbance calculation region is calculated for each wavelength and then plotted.

The absorbance of wells of various sizes can be calculated by allowing the operator specify the absorbance calculation region as he or she desires. Thus, the calculation of absorbance is possible even if wells of different sizes co-exist on the microchamber array. In this case, the absorbance of each well can be calculated by selecting the absorbance calculation region on an individual well basis.

The absorbance display window 78 of FIG. 8 indicates an example of the absorbance spectrum obtained as a result of absorbance calculation. For example, when the activity or inactivity of cells is read, the solid line indicates the absorbance spectrum obtained from an active cell, while the broken line indicates the absorbance spectrum obtained from an inactive cell. Thus, it can be determined whether a cell is active or not based on the value of absorbance at the peak wavelength of the obtained absorbance spectrum. Further, there are cases where the value of the absorbance is the same but the peak position is shifted.

The absorbance of the zero-correction solvent and the tested sample is calculated in the following manner. Initially, absorbance is calculated for all of the pixels constituting the well designated as the absorbance calculation region at a certain wavelength, in accordance with the following equation (1):

$$Abs = \log(1/T) \qquad (1)$$

$$T = E_t/E_0$$

wherein

T: transmittance $E_t$: the readout value of the tested sample readout result $E_0$: the readout value of the zero-correction solvent readout result Abs: absorbance.

Thereafter, the average of the calculated absorbance is determined to obtain an average absorbance at the certain wavelength.

This calculation of absorbance is performed on all of the wavelengths in the readout result 411 in the database, so that the absorbance for each wavelength is calculated and then plotted.

Figure 13:
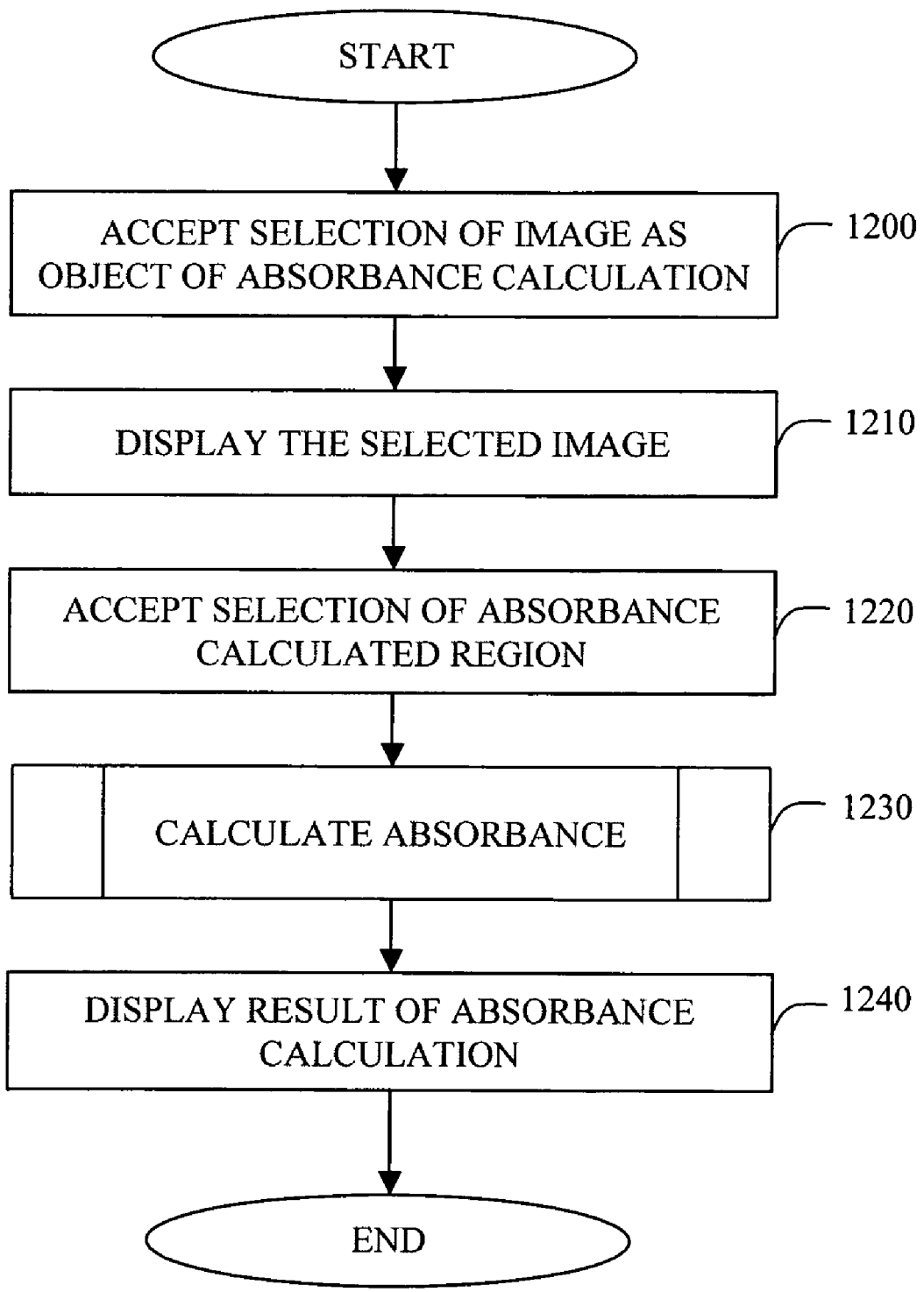
FIG. 13 is a flowchart of an absorbance calculation process.

FIG. 13 shows a flowchart of the process performed by the absorbance calculation program 32.

In FIG. 13, after the start of operation, the entry of selection of the image as the object of calculation of absorbance is accepted from the operator (step 1200). Then, the selected image is displayed (step 1210). The entry of selection of an absorbance calculation region is accepted (step 1220), the absorbance is calculated by running the absorbance calculation sub-routine shown in FIG. 14 (step 1230), and the result is displayed (step 1240).

Figure 14:
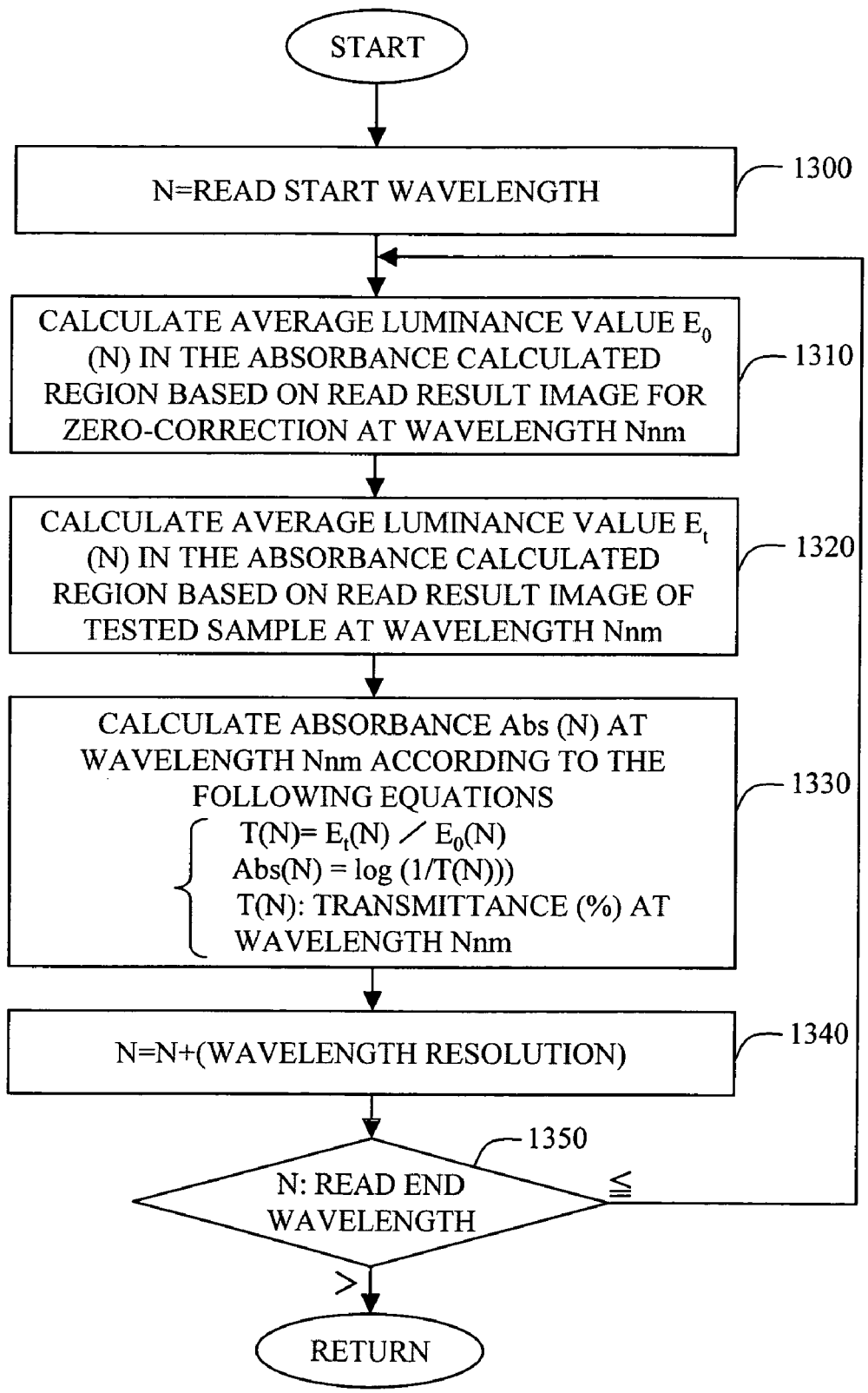
FIG. 14 is a flowchart of an absorbance calculation sub-routine.

FIG. 14 shows a flowchart of the process of absorbance calculation.

Initially, the readout start wavelength is set in variable N (step 1300). Next, an average absorbance $E_0$ (N) and $E_t$ (N) are calculated for the zero-correction readout result image and the sample readout result image at a wavelength N nm, respectively (steps 1310 and 1320). Then, an absorbance Abs (N) at the wavelength N nm is calculated based on $E_0$ (N) and $E_t$ (N) (step 1330). Next, a value corresponding to the wavelength resolution is added to variable N. Thereafter, if N is equal to or smaller than the readout end wavelength, the routine returns to step 1310 and the process is repeated. If N is larger than the readout end wavelength, the process comes to an end and the routine returns to step 1230 in FIG.

13. After the absorbance calculated in FIG. 14 is displayed (step 1240), the process is completed.

Hereafter, the optical path length correction process will be described.

Figure 24:
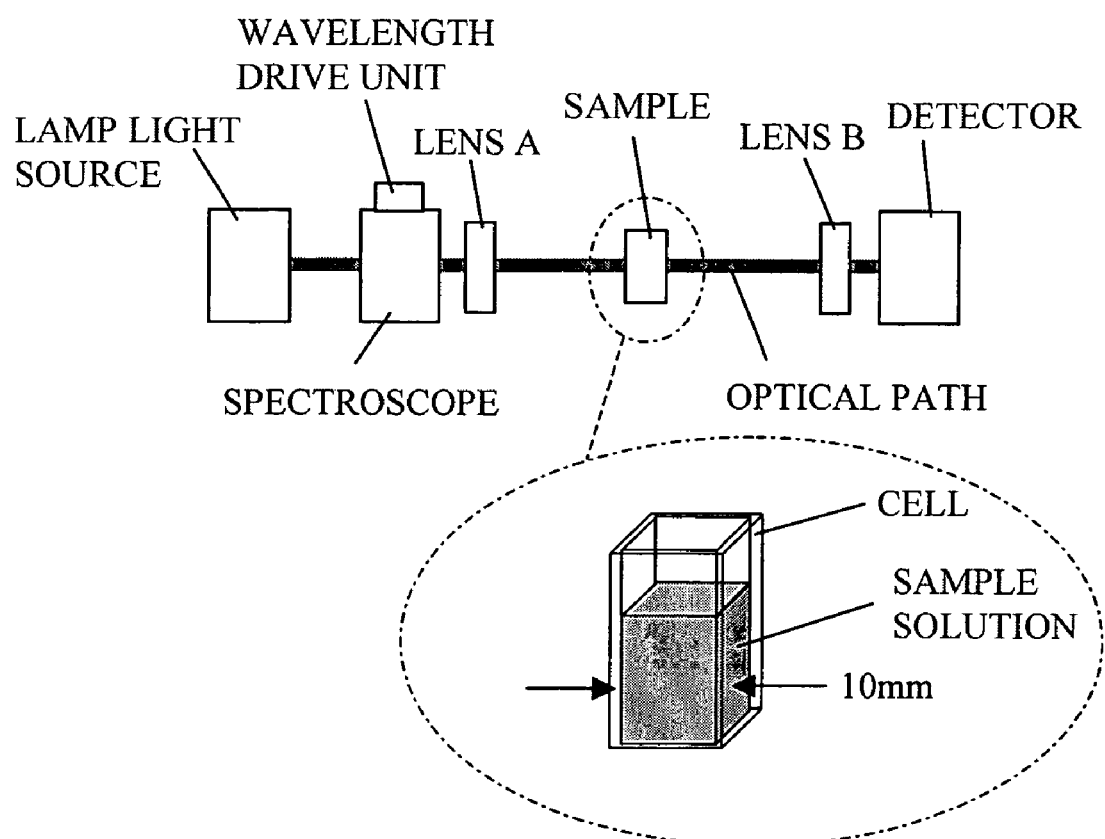
FIG. 24 schematically shows the optical system of a conventional absorbance reading apparatus.

The commercially available conventional absorptiometers calculate absorbance according to the equation (1), as does the system according to the invention. The optical path length in the commercially available absorptiometers is the width of the cell (see FIG. 24), which is generally 10 mm. On the other hand, the optical path length in the system of the invention is the depth of the wells in the microchamber array. Namely, the optical path length is the distance of travel of light through the sample that is being read.

In general, the relationship between the absorbance (Abs) and the optical path length is expressed by the following equation (2):

$$Abs = C \times L \times M \qquad (2)$$

wherein
C: molar absorbance coefficient
L: optical path length
M: concentration.

The molar absorbance coefficient is an inherent coefficient of the sample, and it is given for each biological sample. The concentration is the concentration of the sample. Thus, it can be seen from the equation (2) that the absorbance is proportional to the optical path length. Namely, the absorbance for the optical path length of 10 mm can be determined based on the absorbance obtained by the system of the invention by taking the ratio of the depth L (μm) of the wells and the cell width 10 mm of the conventional absorptiometer into consideration as a coefficient. Accordingly, the absorbance obtained in the system of the invention can be compared with that obtained in the conventional absorptiometer without any correction.

Figure 15:
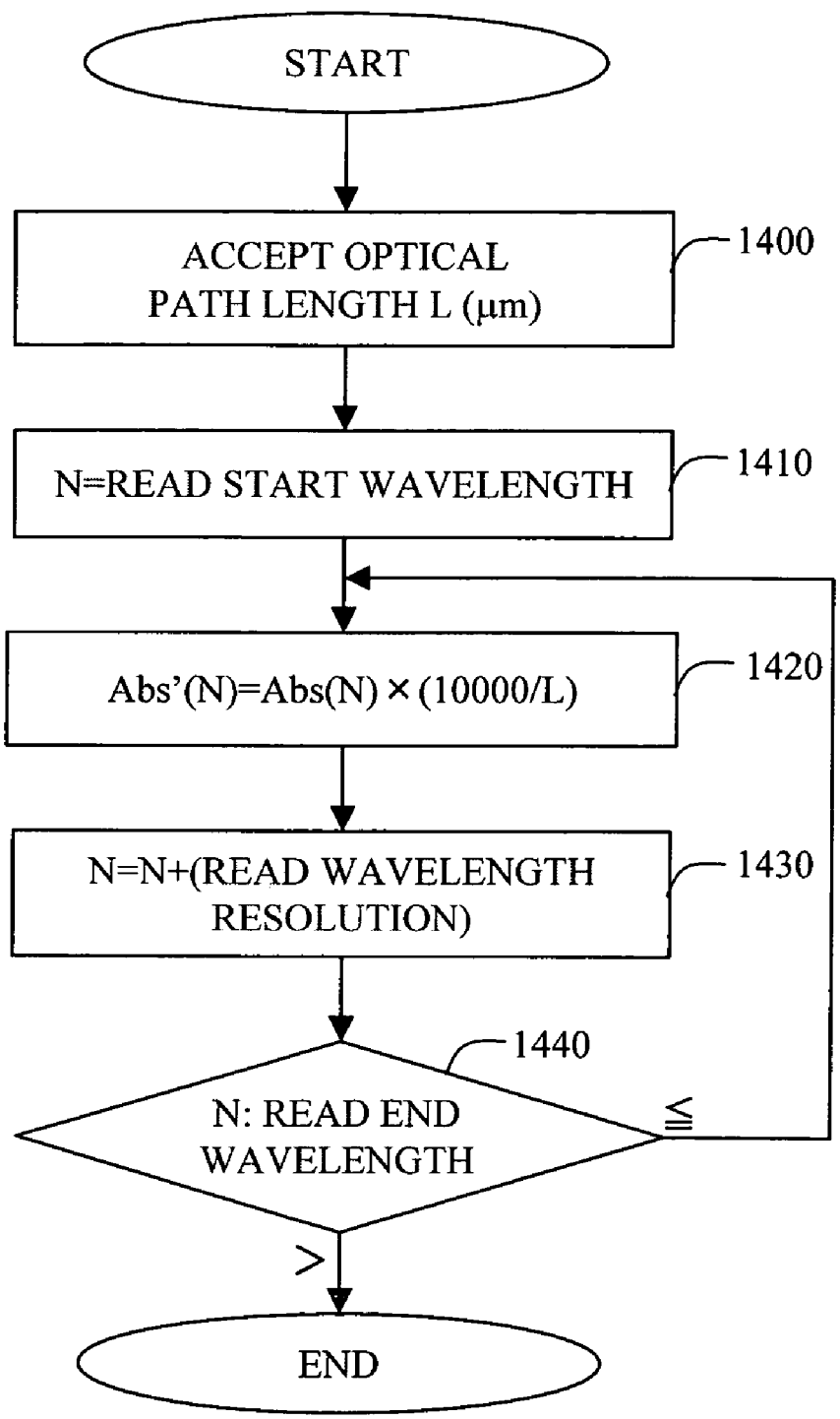
FIG. 15 is a flowchart of an optical path length correction process.

FIG. 15 shows a flowchart of the optical path length correction process.

In the absorbance readout system according to the invention, absorbance is corrected by the equation in step 1420. In the equation, L is the depth of the wells in the microchamber array and is entered by the operator as a parameter.

After the start of the optical path length correction process, the absorbance calculation program 32 accepts the optical path length L (μm), which is the depth of the wells in the microchamber array used in the readout (step 1400). The readout start wavelength is set in the variable N (step 1410). Then, the absorbance Abs (N) at the wavelength N before correction is obtained, and an absorbance Abs' (N) at the wavelength N after correction is obtained based on the optical path length L (step 1420). Thereafter, the readout wavelength resolution is added to the variable N (step 1430). If N is equal to or smaller than the readout end wavelength, the routine returns to step 1420 and the process is repeated, while if N is larger than the readout end wavelength, the process comes to an end (step 1440). In this manner, the optical path length is corrected for all of the wavelengths that have been read. The absorbance after correction is stored in a table of absorbance and wavelengths in the database 4, as it is before correction.

Hereafter, the microchamber array will be described.

Figure 16:
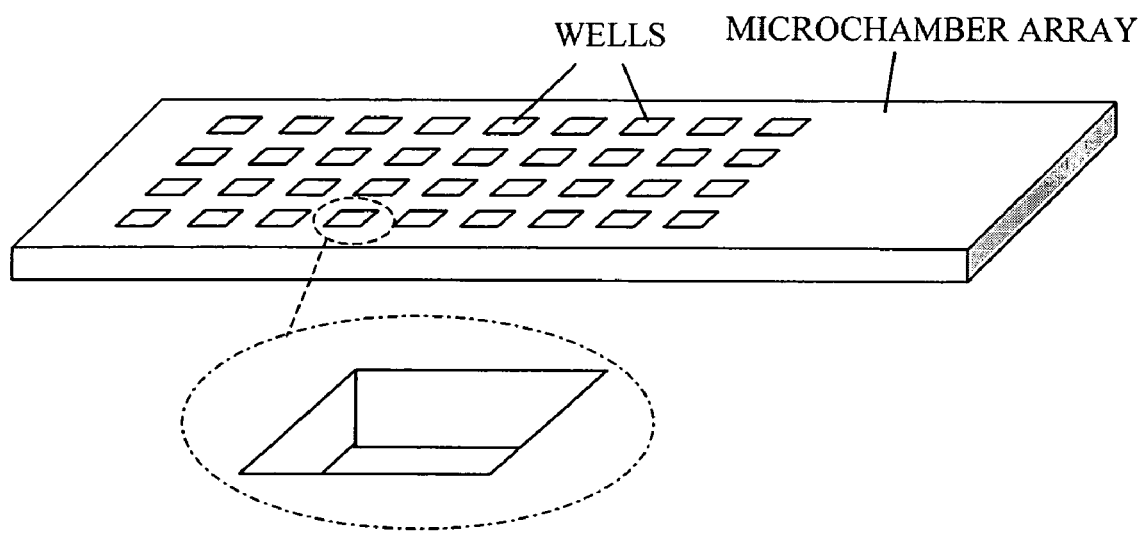
FIG. 16 shows a conceptual diagram of a microchamber array (Example 1).

FIG. 16 schematically shows a microchamber array, which is a slide glass substrate (25 mm×75 mm, thickness 1 mm) on which microsize wells are formed. The dimensions of the wells are on the order of 80 to several hundred μm in both length of each side and depth. The upper surface of the microchamber array on which the wells are formed will be referred to as a first plane, the bottom surface will be referred to as a second plane. In the wells on the first plane are poured biological samples such as cells. Human cells have dimensions on the order of 10 to 20 μm, while animal or plant cells have dimensions of several hundred μm. The size of the well is based on the size of cells, because each well is supposed to house one cell. After the cells are injected into the wells, a reaction solution is allowed to drip onto the cells that have been injected, i.e., the tested samples. The reaction solution thus reacts with the cells. Thus, the microchamber array is capable of processing the analysis of great amounts of tested samples at once (i.e., high throughput), thereby advantageously reducing the amount of time for analysis and the amount of reagents required with the resultant reduction of cost.

When cells are used as samples, it is preferable to use a microchamber array with the size of each well in the ranges between 0.03 to 1 mm in length and between 0.03 to 1 mm in width, and the distance between adjacent wells in the range between 0.03 to 1 mm. The number of wells provided in a single microchamber array is preferably more than 100 and not more than 10,000.

Figure 17:
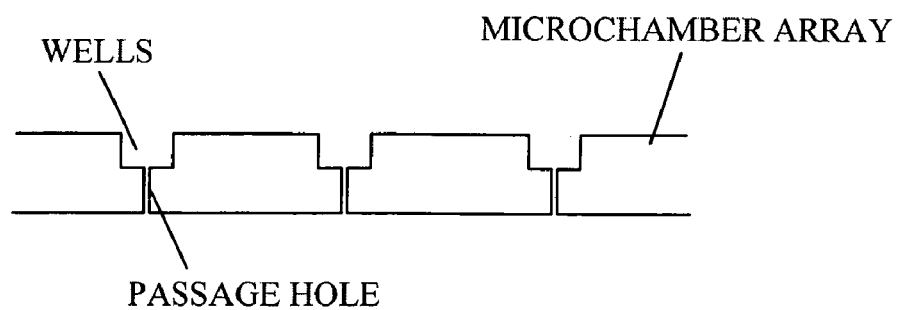
FIG. 17 shows a conceptual diagram of a microchamber array (Example 2).
Figure 18A:
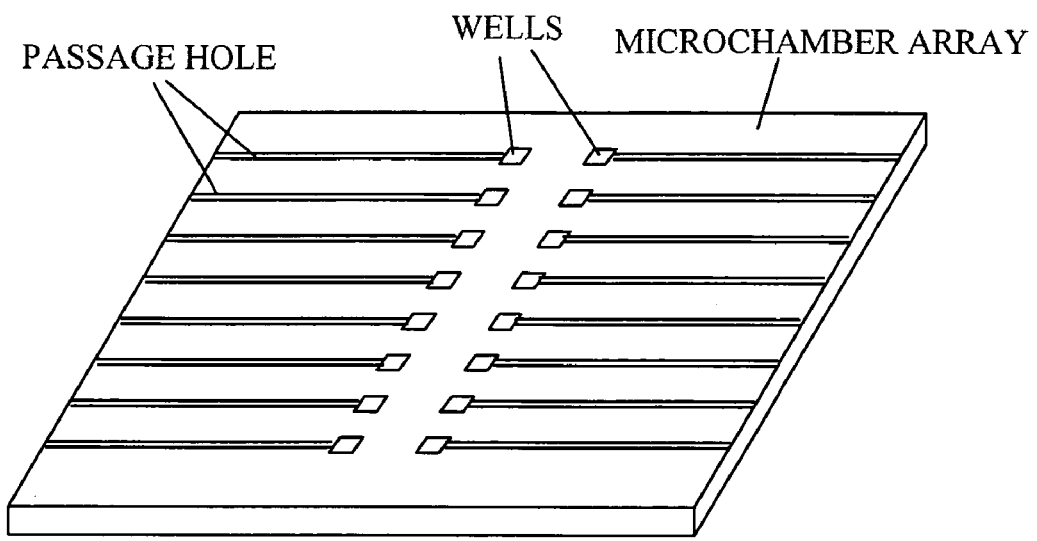
FIG. 18 shows a conceptual diagram of a microchamber array (Example 3).
Figure 18B:
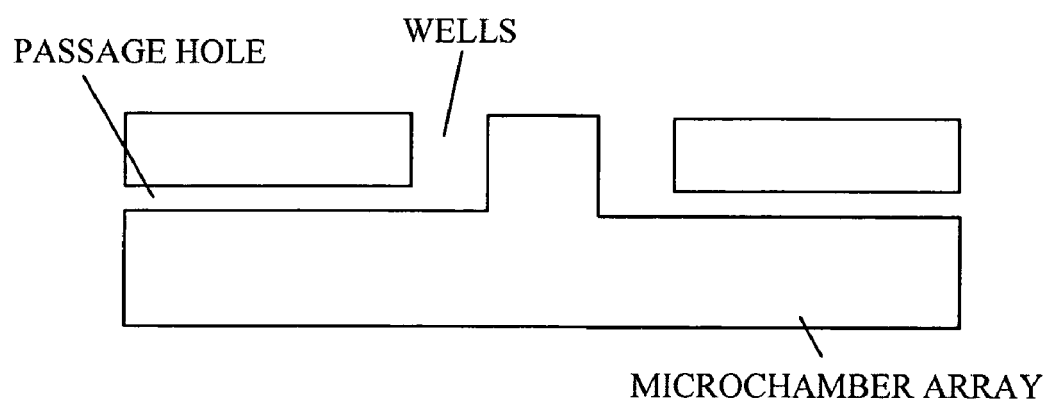

Other examples of the microchamber array are also conceivable, in addition to the one shown in FIG. 16. FIG. 17 shows an example of the microchamber array in which the bottom surface of each well is provided with a passage hole. The size of the microchamber array and that of the wells are similar to those of the example shown in FIG. 16, and the passage opening is 10 μm in diameter. FIG. 18 shows the concept of a microchamber array in which a passage opening is provided on the side of each well. FIG. 18(a) is a perspective view of the microchamber array. Wells are arranged in two columns on the microchamber array. FIG. 18(b) shows a cross-section of the microchamber array.

Hereafter, the recovery of samples will be described.

Figure 19:
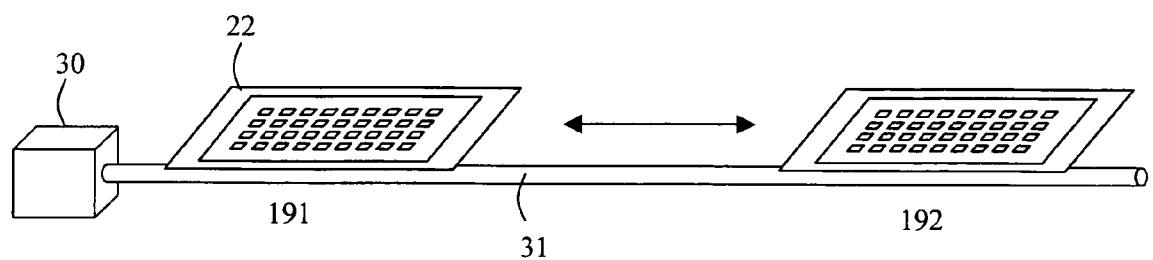
FIG. 19 shows a diagram illustrating the recovery of a sample.

FIG. 19 illustrates the shifting of the sample base 22. The sample base 22 and the microchamber array, when they are read, are controlled to be located at a readout position 191 by the processing unit. As the sample recovery program 33 is activated, the sample base 22 and the microchamber array are shifted to a sample recovery position 192 by the program. The sample base 22 and the microchamber array are shifted by controlling the sample base motor 30 and the ball screw A 31.

Figure 20:
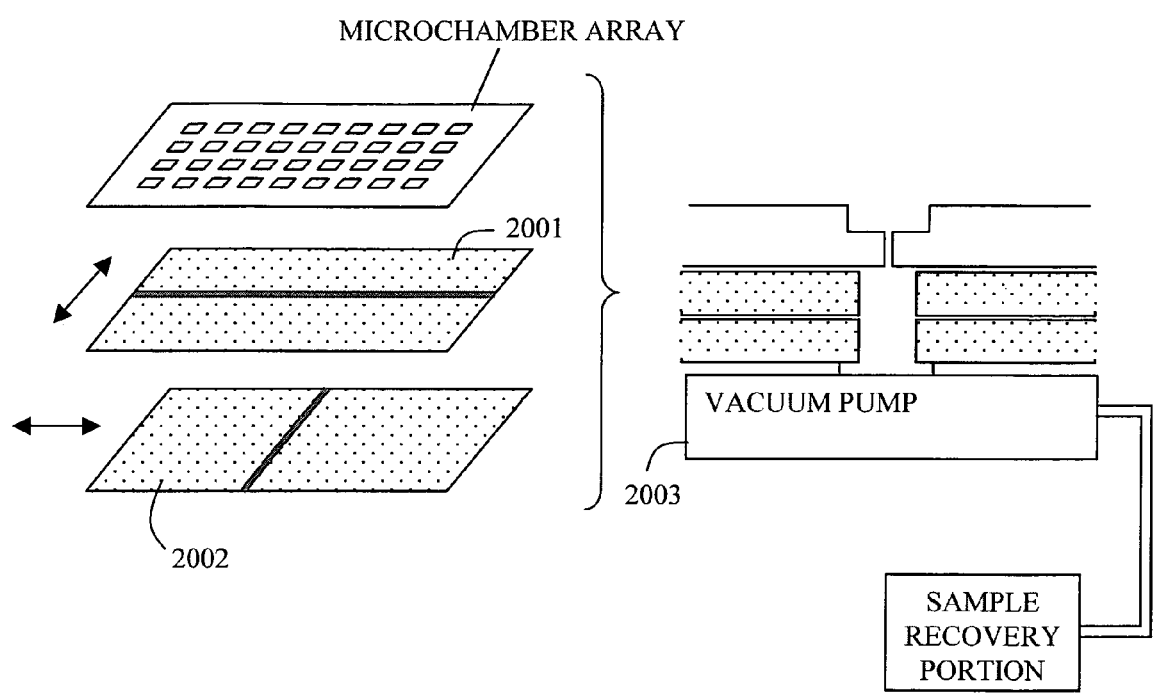
FIG. 20 shows a diagram of a sample recovery mechanism (Example 1).

FIG. 20 schematically illustrates the principle of the sample recovery mechanism 28. The sample recovery mechanism 28 is comprised of a horizontal-axis recovery panel 2001, a vertical-axis recovery panel 2002, and a vacuum pump 2003. The horizontal-axis recovery panel 2001 has openings along horizontal lines. The vertical-axis recovery panel 2002 has openings along vertical lines. The horizontal- and vertical-axis recovery panels 2001 and 2002 are disposed below the microchamber array, and a vacuum pump 2003 is disposed further below. Thus, the samples can be recovered from any desired well to the sample recovery portion by the sucking operation of the vacuum pump 2003.

In the case of the microchamber array shown in FIG. 17, an tested sample in a desired well on the microchamber array can be recovered by controlling the vertical direction position of the horizontal-axis recovery panel 2001 and the horizontal direction position of the vertical-axis recovery panel and then sucking by the vacuum pump 2003.

Figure 21:
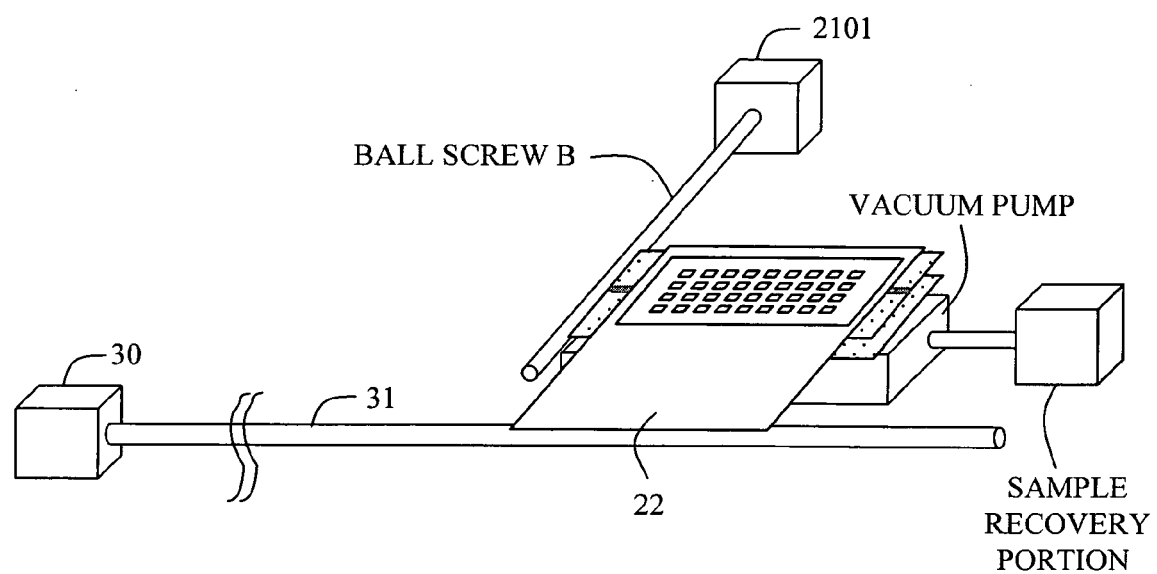
FIG. 21 shows a diagram of a sample recovery mechanism (Example 2).

FIG. 21 shows an example in which the horizontal-axis recovery panel is controlled by a horizontal-axis recovery panel motor 2101 and a ball screw B. The position of the vertical-axis recovery panel is fixed. The horizontal-axis direction of the microchamber array is controlled by a sample base motor 30 and a ball screw A31.

Figure 22:
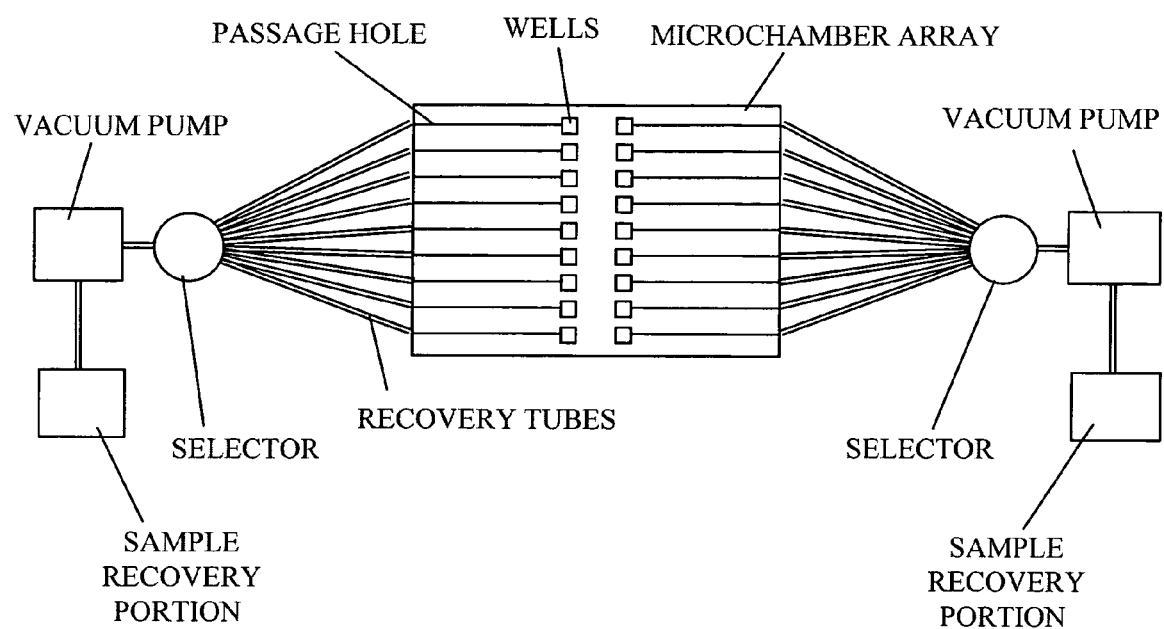
FIG. 22 shows a diagram of a sample recovery mechanism (Example 3).

FIG. 22 shows a concept diagram illustrating the principle of the sample recovery mechanism in the microchamber array shown in FIG. 18. In FIG. 22, the sample recovery mechanism is comprised of recovery tubes, a selector, and a vacuum pump. The selector and the vacuum pump are controlled by the processing unit, such that the selector selects one of the recovery tubes for recovering the sample in accordance with the well designated by the sample recovery program 33. Then, the vacuum pump sucks to recover the sample in a desired well into the sample recovery portion.

Figure 23:
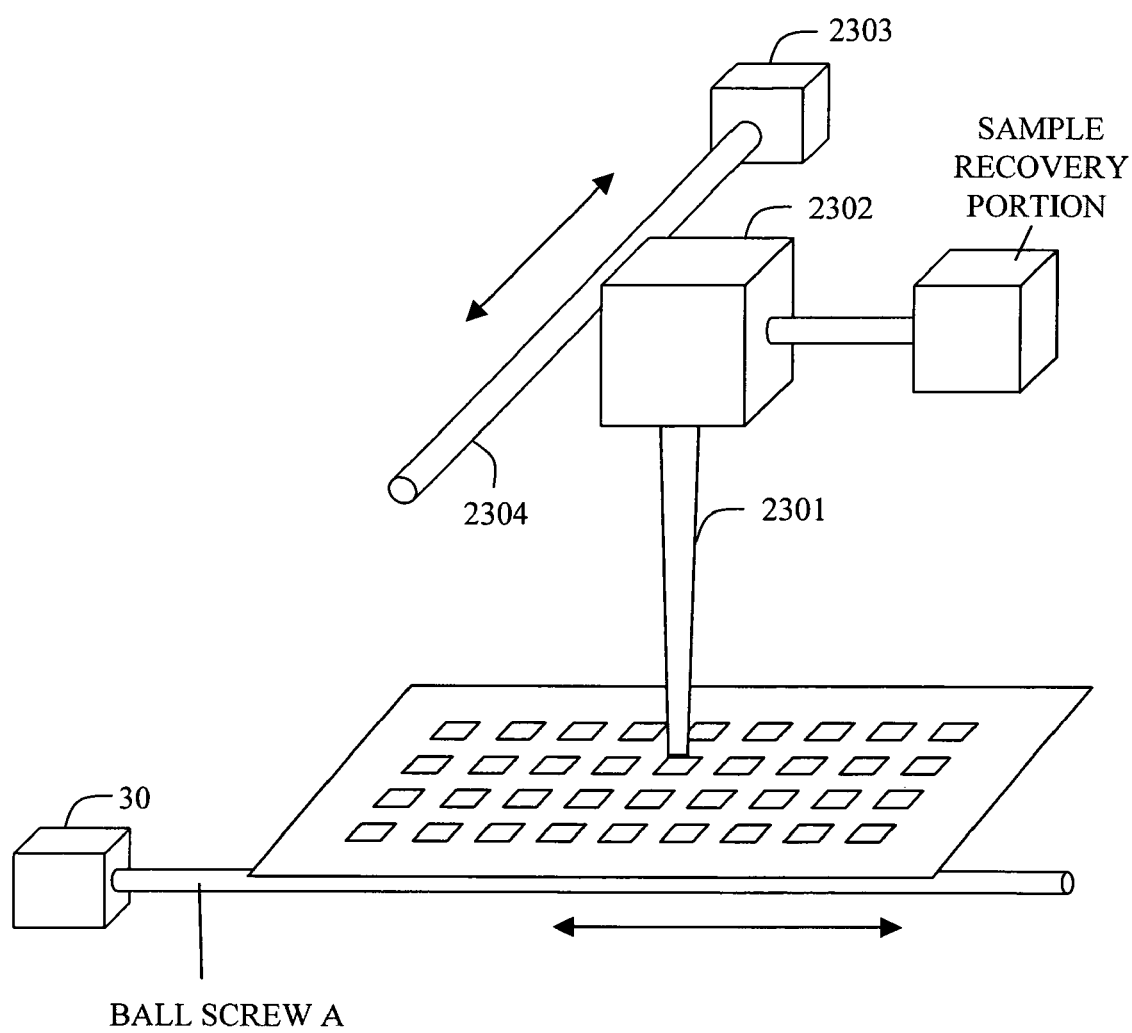
FIG. 23 shows a diagram illustrating a sample recovery mechanism.

FIG. 23 shows a concept diagram illustrating the principle of the sample recovery mechanism in the microchamber array shown in FIG. 16. In FIG. 23, the sample recovery mechanism is comprised of a microsyringe 2301, a vacuum pump 2302, a syringe motor 2303, and a ball screw C2304. The horizontal direction of the microchamber array is controlled by the sample base motor 30 and the ball screw A. The vertical direction of the microsyringe 2301 is controlled by the syringe motor 2303 and the ball screw C2304. The microsyringe 2301 is thus moved to a desired well on the microchamber array, so that the sample in the desired well can be sucked by the vacuum pump 2302 and recovered.

The calculation of absorbance of tested samples using the microchamber array can be applied to research into the mechanism of development of viral diseases and diagnosis and treatment of such diseases. Viruses deliver their own genes into the gene of an infected cell and destroy the cell. It is necessary to examine whether or not a viral gene exists in a particular cell and, if so, how much of it exits in what state, for individual cells. Using the microchamber array, individual cells can be analyzed at high throughput and very effectively.

The present invention relates to an apparatus for reading out absorbance for each well on a microchamber array which, as a prerequisite, must be made of a transparent material. In the present invention, the samples to be injected into the wells include DNA and proteins as well as cells.

INDUSTRIAL APPLICABILITY

Thus, in accordance with the absorbance reading system constructed as described above, the absorbance of each of a number of wells on the microchamber array can be read in great quantities at once and at high speed. Because a telecentric lens is employed in the optical system for focusing transmitted light from a sample onto the CCD camera, readouts can be obtained at high positional accuracy. The system is capable of reading the absorbance of wells of various sizes provided on the microchamber array. Based on the result of absorbance calculation, the user can recover a tested sample in an arbitrary well for more detailed analysis.

The invention claimed is:

1. An absorbance reading apparatus for reading the absorbance of a sample injected into each of a plurality of wells provided on a microchamber array, the apparatus comprising:
    a sample base for mounting the microchamber array;
    a light source;
    a spectroscope on which light from the light source is incident;
    an irradiation optical system for adjusting the distribution of luminance of irradiation light emerging from the spectroscope;
    a field lens for enlarging the size of irradiation light transmitted by the irradiation optical system and irradiating the microchamber array mounted on the sample base with the enlarged irradiation light;
    a one-side telecentric optical system for receiving sample-transmitted light; and
    an imaging camera for producing image data based on the sample-transmitted light received via the one-side telecentric optical system.

2. The absorbance reading apparatus according to claim 1, further comprising a mirror for guiding the irradiation light transmitted by the irradiation optical system such that the microchamber array is irradiated in the direction from a second plane toward a first plane, or from the first plane to the second plane.

3. The absorbance reading apparatus according to claim 1, further comprising a sample recovery mechanism for recovering a sample in a well.

4. The absorbance reading apparatus according to claim 1, wherein the absorbance of a well on the microchamber array is read within one minute.

* * * * *

UNITED STATES PATENT AND TRADEMARK OFFICE
CERTIFICATE OF CORRECTION

PATENT NO. : 7,362,433 B2  Page 1 of 1
APPLICATION NO. : 10/550004
DATED : April 22, 2008
INVENTOR(S) : Tamiya et al.

It is certified that error appears in the above-identified patent and that said Letters Patent is hereby corrected as shown below:

On the Title of the patent, Under Item (54) please DELETE:

"Absorbance Reader Apparatus, Absorbance Reader Control Method, and Absorbance Calculation Program"

and ADD:

--Absorbance Reading Apparatus, Absorbance Reading Control Method, and Absorbance Calculation Program--

Signed and Sealed this

Second Day of June, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,362,433 B2  Page 1 of 1
APPLICATION NO. : 10/550004
DATED : April 22, 2008
INVENTOR(S) : Tamiya et al.

It is certified that error appears in the above-identified patent and that said Letters Patent is hereby corrected as shown below:

On the Title Page of the patent, Under Item (54) and Column 1, lines 1-4, please DELETE:

"Absorbance Reader Apparatus, Absorbance Reader Control Method, and Absorbance Calculation Program"

and ADD:

--Absorbance Reading Apparatus, Absorbance Reading Control Method, and Absorbance Calculation Program--

This certificate supersedes the Certificate of Correction issued June 2, 2009.

Signed and Sealed this

Twenty-third Day of June, 2009

JOHN DOLL
*Acting Director of the United States Patent and Trademark Office*